(12) United States Patent
Himmelsbach et al.

(10) Patent No.: US 7,662,790 B2
(45) Date of Patent: Feb. 16, 2010

(54) GLUCOPYRANOSYL-SUBSTITUTED (HETEROARYLOXY-BENZYL)-BENZENE DERIVATIVES, MEDICAMENTS CONTAINING SUCH COMPOUNDS, THEIR USE AND PROCESS FOR THEIR MANUFACTURE

(75) Inventors: Frank Himmelsbach, Mittelbiberach (DE); Matthias Eckhardt, Biberach (DE); Peter Eickelmann, Mittelbiberach (DE); Leo Thomas, Biberach (DE)

(73) Assignee: Boehringer Ingelheim International GmbH, Ingelheim (DE)

(*) Notice: Subject to any disclaimer, the term of this patent is extended or adjusted under 35 U.S.C. 154(b) by 339 days.

(21) Appl. No.: 11/403,444

(22) Filed: Apr. 13, 2006

(65) Prior Publication Data
US 2006/0234953 A1   Oct. 19, 2006

(30) Foreign Application Priority Data
Apr. 15, 2005   (EP)   ................... 05008273

(51) Int. Cl.
A61K 31/7034 (2006.01)
A61K 31/33 (2006.01)
C07H 1/00 (2006.01)
C07H 7/04 (2006.01)
C07D 315/00 (2006.01)

(52) U.S. Cl. .................. 514/23; 514/460; 549/417; 536/1.11

(58) Field of Classification Search .............. None
See application file for complete search history.

(56) References Cited

U.S. PATENT DOCUMENTS

| | | | |
|---|---|---|---|
| 4,602,023 A | 7/1986 | Kiely et al. |
| 4,786,023 A | 11/1988 | Harris et al. |
| 4,786,755 A | 11/1988 | Kiely et al. |
| 6,414,126 B1 | 7/2002 | Ellsworth et al. |
| 6,515,117 B2 | 2/2003 | Ellsworth et al. |
| 6,627,611 B2 | 9/2003 | Tomiyama et al. |
| 6,774,112 B2 | 8/2004 | Gougoutas |
| 6,936,590 B2 | 8/2005 | Washburn et al. |
| 7,169,761 B2 | 1/2007 | Tomiyama et al. |
| 7,202,350 B2 | 4/2007 | Imamura et al. |
| 7,371,732 B2 | 5/2008 | Eickelmann et al. |
| 7,375,090 B2 | 5/2008 | Himmelsbach et al. |
| 7,393,836 B2 | 7/2008 | Eckhardt et al. |
| 7,417,032 B2 | 8/2008 | Eckhardt et al. |
| 7,419,959 B2 | 9/2008 | Eckhardt et al. |
| 7,579,449 B2 | 8/2009 | Eckhardt et al. |
| 2002/0137903 A1 | 9/2002 | Ellsworth et al. |
| 2003/0064935 A1 | 4/2003 | Gougoutas |
| 2003/0114390 A1 | 6/2003 | Washburn et al. |
| 2004/0138148 A1 | 7/2004 | Fushimi et al. |
| 2004/0138439 A1 | 7/2004 | Deshpande et al. |
| 2005/0065098 A1 | 3/2005 | Fujikura et al. |
| 2005/0124555 A1 | 6/2005 | Tomiyama et al. |
| 2005/0209166 A1 | 9/2005 | Eckhardt et al. |
| 2006/0019948 A1 | 1/2006 | Eckhardt et al. |
| 2006/0035841 A1 | 2/2006 | Eckhardt et al. |
| 2006/0063722 A1 | 3/2006 | Washburn et al. |
| 2006/0142210 A1 | 6/2006 | Eckhardt et al. |
| 2006/0189548 A1 | 8/2006 | Himmelsbach et al. |
| 2006/0234953 A1 | 10/2006 | Himmelsbach et al. |
| 2006/0251728 A1 | 11/2006 | Himmelsbach et al. |
| 2006/0258749 A1 | 11/2006 | Eckhardt et al. |
| 2007/0004648 A1 | 1/2007 | Himmelsbach et al. |
| 2007/0027092 A1 | 2/2007 | Himmelsbach et al. |
| 2007/0049537 A1 | 3/2007 | Eckhardt et al. |
| 2007/0054867 A1 | 3/2007 | Eckhardt et al. |
| 2007/0073046 A1 | 3/2007 | Eckhardt et al. |
| 2007/0249544 A1 | 10/2007 | Himmelsbach et al. |
| 2007/0259821 A1 | 11/2007 | Eckhardt et al. |
| 2008/0058379 A1 | 3/2008 | Eckhardt et al. |
| 2009/0023913 A1 | 1/2009 | Eckhardt et al. |

FOREIGN PATENT DOCUMENTS

| | | |
|---|---|---|
| CA | 2 388 818 A1 | 5/2001 |
| CA | 2 494 177 A1 | 2/2004 |
| CA | 2 508 024 A1 | 6/2004 |
| CA | 2 508 226 A1 | 6/2004 |

(Continued)

OTHER PUBLICATIONS

Adachi et al., "T-1095, a Renal Na+-Glucose Transporter Inhibitor, Improves Hyperglycemia in Streptozotocin-Induced Diabetic Rats" Metabolism (2000) vol. 49, No. 8, pp. 990-995.*

(Continued)

*Primary Examiner*—Shaojia Anna Jiang
*Assistant Examiner*—Eric S Olson
(74) *Attorney, Agent, or Firm*—Michael P. Morris; Edouard G. Lebel; David A. Dow

(57) ABSTRACT

Glucopyranosyloxy-substituted (heteroaryloxy-benzyl)-benzene compounds of the general formula I

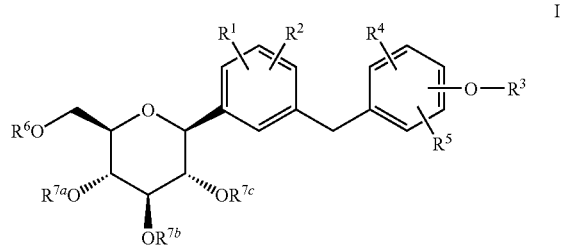

where the groups $R^1$ to $R^6$ as well as $R^{7a}$, $R^{7b}$, $R^{7c}$ are defined according to claim 1, including the tautomers, the stereoisomers thereof, the mixtures thereof and the salts thereof. The compounds according to the invention are suitable for the treatment of metabolic disorders.

18 Claims, No Drawings

FOREIGN PATENT DOCUMENTS

| | | |
|---|---|---|
| CA | 2 557 269 A1 | 9/2005 |
| CA | 2 557 320 A1 | 9/2005 |
| CA | 2 557 801 A1 | 10/2005 |
| CA | 2 573 777 A1 | 2/2006 |
| EP | 0 206 567 A2 | 6/1986 |
| EP | 1344369 A1 | 9/2003 |
| EP | 1 385 856 A0 | 2/2004 |
| EP | 1224195 B | 5/2005 |
| EP | 1 553 094 A1 | 7/2005 |
| EP | 1 609 785 A1 | 12/2005 |
| JP | 58/164502 A | 9/1983 |
| JP | 62/030750 A | 2/1987 |
| JP | 11/124392 A | 5/1999 |
| JP | 2001/288178 A | 10/2001 |
| JP | 2003/811458 A | 3/2003 |
| JP | 2005/359630 A | 12/2004 |
| WO | WO 98/31697 | 7/1998 |
| WO | WO 01/27128 A1 | 4/2001 |
| WO | 01/74834 A1 | 10/2001 |
| WO | 02/064606 A1 | 8/2002 |
| WO | WO 02/083066 A2 | 10/2002 |
| WO | WO 03/099836 A1 | 12/2003 |
| WO | WO 2004013118 A1 | 2/2004 |
| WO | WO 2004/052902 A1 | 6/2004 |
| WO | WO 2004/052903 A1 | 6/2004 |
| WO | WO 2004/063209 A2 | 7/2004 |
| WO | 2004/076470 A2 | 9/2004 |
| WO | WO 2004/080990 A1 | 9/2004 |
| WO | 2005/012326 A1 | 1/2005 |
| WO | 2005/012318 A2 | 2/2005 |
| WO | 2005/085237 A1 | 9/2005 |
| WO | 2005/085265 A1 | 9/2005 |
| WO | WO 2005/092877 A1 | 10/2005 |
| WO | 2006/011469 A1 | 2/2006 |
| WO | 2006/034489 A2 | 3/2006 |
| WO | 2006/064033 A2 | 6/2006 |
| WO | 2006/089872 A1 | 8/2006 |
| WO | 2006/108842 A1 | 10/2006 |
| WO | 2006/117360 A1 | 11/2006 |
| WO | 2006/120208 A1 | 11/2006 |
| WO | 2007/014894 A2 | 2/2007 |
| WO | 2007/025943 A2 | 3/2007 |
| WO | 2007/028814 A1 | 3/2007 |
| WO | 2007/031548 A2 | 3/2007 |

OTHER PUBLICATIONS

International Search Report for PCT/EP2006/061520 mailed Jul. 26, 2006.

Benhaddou, Rachida., et al; Tetra-n-Propylammonium Tetra-Oxoruthenate(VII): A Reagent of Choice for the Oxidation of Diversely Protected Glycopyranoses and Glycofuranoses to Lactones; Carbohydrate Research (1994) vol. 260 pp. 243-250.

Dohle, Wolfgang., et al; Copper-Mediated Cross-Coupling of Functionalized Arylmagnesium Reagents with Functionalized Alkyl and Benzylic Halides; Organic Letters (2001) vol. 3 No. 18 pp. 2871-2873.

Fuerstner, Alois., et al; Practical Method for the Rhodium-Catalyzed Addition of Aryl- and Alkenylboronic Acids to Aldehydes; Advanced Synthesis and Catalysis (2001) vol. 343 No. 4 pp. 343- 350.

Hatsuda, Asanori., et al; A Practical Synthesis of Highly Functionalized Aryl Nitriles Through Cyanation of Aryl Bromides Employing Heterogeneous Pd/C; Tetrahedron Letters (2005) vol. 46 pp. 1849-1853; Elsevier Ltd.

Hutton, Craig A., et al; A Convenient Preparation of dityrosine Via Miyaura Borylation-Suzuki Coupling of Iodotyrosine Derivatives; Tetrahedron Letters (2003) vol. 44 pp. 4895-4898; Pergamon Press.

Iida, Takehiko., et al; Tributylmagnesium Ate Complex-Mediated Novel Bromine-Magnesium Exchange Reaction for Selective Monosubstitution of Dibromoarenes; Tetrahedron Letters (2001) vol. 42 pp. 4841-4844; Pergamon Press.

Jagdmann Jr, G. Erik; Synthesis of 5-(4-Substituted Benzyl)-2,4-Diaminoquinazolines as Inhibitors of Candida Albicans Dihydrofolate Reductase; Journal Heterocyclic Chemical (1995) vol. 32 pp. 1461-1465.

Koo, Ja Seo., et al; 2-Pyridyl Cyanate: A Useful Reagent for he Preparation of Nitriles; Synthetic Communications (1996) vol. 26 No. 20 pp. 3709-3713; Marcel Dekker, Inc.

Kuribayashi, Takeshi., et al; c-Glycosylated Aryl tins: Versatile Building Blocks for Aryl C-Glycoside Glycomimetics; J. Carbohydrate Chemistry (1999) vol. 18, No. 4 pp. 371-382.

Kuribayashi, Takeshi., et al; C-Glycosylated Diphenylmethanes and Benzophenones: The Stille Coupling Reaction of C-Glycosylated Aryl tins with Benzyl Bromides and Acid Chlorides; J. Carbohydrate Chemistry (1999) vol. 18, No. 4 pp. 393-401.

Kuribayashi, Takeshi., et al; Bis C-Glycosylated Diphenylmethanes for Stable Glycoepitope Mimetics; Syntletters (1999) vol. 6 pp. 737-740.

Langle, Sandrine., et al; Selective Double Suzuki Cross-Coupling Reactions. Synthesis of Unsymmetrical Diaryl (or Heteroaryl) Methanes; Tetrahedron Letters (2003) vol. 44 pp. 9255-9258; Pergamon Press.

Mclaughlin, Mark., et al; Suzuki-Miyaura Cross-Coupling of Benzylic Phosphahates with Arylboronic Acids; Organic Letters (2005) vol. 7 No. 22 pp. 4875-4878.

Neamati, Ouri., et al;, "Depsides and Depsidones as Inhibiton of HIV-1 Integrase: Dimvery of Novel Inhibitors Through 3D Database Searclung", J. Med. Chem., 1997, vol. 40, pp. 942-951.

Nobre, Sabrina M., et al; Synthesis of Diarylmethane Derivatives from Pd-Catalyzed Cross-Coupling Reactions of Benzylic Halides with Arylboronic Acids; Tetrahedron Letters (2004) vol. 45.

Oku, Akira., et al; T-1095, An Inhibitor or renal $Na^+$ -Glucose Cotransporters, May Provide a Novel Approach to Treating Diabetes; Diabetes (1999) vol. 48 pp. 1794-1800.

Perner, Richard J., et al; 5,6,7-Trisubstituted 4-Aminopyrido[2,3-d]pyrimidines as Novel inhibitors of Adenosime Kinase; Journal of Medicinal Chemistry (2003) vol. 46 pp. 5249-5257.

Sommer, Michael Bech., et al; displacement of Halogen of 2-Halogeno-Substituted Benzonitriles with Carbonions. Preparation of (2-Cyanoaryl)arylacetonitriles; Journal of Organic Chemistry (1990) vol. 55 pp. 4817-4821.

Revesz, Lasslo., et al; SAR of Benzoylpylpyridines and Benzophenones as p38 Alpha MAP Kinase Inhibitors with Oral Activity; Bioorganic & Medicinal Chemistry Letters (2004) vol. 14 pp. 3601-3605.

Stazi, Federica., et al; Statistical Experimental Design-Driven Discovery of room-Temperature Conditions for Palladium-Catalyzed Cyanation of Aryl Bromides; Tetrahedron Letters (2005) vol. 46 1815-1818; Elsevier Ltd.

Tykwinski, Rik R; Evolution in the Palladium-Catalyzed Cross-Coupling of sp- and sp2-Hybridized Carbon Atoms; Angew Chemical International Edition (2003) vol. 42 pp. 1566-1568.

Ueta, Kiichiro., et al; Long-Term Treatment with the $Na^+$ -Glucose Cotransporter Inhibitor T-1095 Causes Sustained Improvement in Hyperglycemia and Prevents Diabetic Neuropathy in Goto-Kakizaki Rats; Life Sciences (2005) vol. 76 pp. 2655-2668.

Wallace, Debra J., et al; Cyclopropylboronic Acid: Synthesis and Suzuki Cross-Coupling Reactions; Tetrahedron Letters (2002) vol. 43 pp. 6987-6990; Pergamon Press.

Xue, Song., et al; Zinc-mediated Synthesis of Alpha-C-Glycosided from 1,2-Anhydroglycosides; Synletters (2003) vol. 6 pp. 870-872.

International Search Report for PCT/EP2005/002618 mailed Jun. 30, 2005.

International Search Report for PCT/EP2006/061956 mailed on Jul. 5, 2006.

International Search report for PCT/EP2006/061957 mailed on Jul. 5, 2006.

International Search Report for PCT/EP2006/062191 mailed Aug. 8, 2006.

International Search Report for PCT/EP2005/056806 mailed Dec. 27, 2006.

International Search Report for PCT/EP2006/066107 mailed Jan. 11, 2007.

International Search Report for PCT/EP2006/066347 mailed Mar. 7, 2007.
International Search Report for PCT/EP2006/065710 mailed Mar. 8, 2007.
International Search Report for PCT/EP2007/051411 mailed on May 2, 2007.
International Search Report for PCT/EP2007/054248 mailed on Jun. 18, 2007.
International Search Report for PCT/EP2006/064702 mailed on Jul. 26, 2007.
Notice of Allowance and Fee(s) Due dated Jan. 13, 2009 from U.S. Appl. No. 11/304,284 filed Dec. 15, 2005.
Non-Final Office Action dated Jun. 24, 2008 from U.S. Appl. No. 11/406,971 filed Apr. 19, 2006.
Non-Final Office Action dated Jun. 5, 2008 from U.S. Appl. No. 11/408,899 filed on Apr. 21, 2006.
Non Final Office Action dated Apr. 2, 2008 from U.S. Appl. No. 11/674,839 filed on Feb. 14, 2007.
Response dated Sep. 25, 2008 to Non-Final Office Action dated Apr. 2, 2008 from U.S. Appl. No. 11/674,839 filed Feb. 14, 2007.
Non-Final Office Action dated May 8, 2008 from U.S. Appl. No. 11/359,846 filed Feb. 22, 2006.
Response dated Nov. 5, 2008 to Non-Final Office Action dated May 8, 2008 from U.S. Appl. No. 11/359,846 filed Feb. 22, 2006.
Notice of Allowance and Fee(s) Due dated Feb. 3, 2009 from U.S. Appl. No. 11/359,846 filed Feb. 22, 2006.
Notice of Allowance and Fee(s) Due dated Dec. 30, 2008 from U.S. Appl. No. 11/674,839 filed Feb. 14, 2007.
Non Final Office Action dated Apr. 2, 2008 from U.S. Appl. No. 11/742,612 filed on May 1, 2007.
Response dated Sep. 25, 2008 to Non-Final Office Action dated Apr. 2, 2008 from U.S. Appl. No. 11/742,612 filed May 1, 2007.
Notice of Allowance and Fee(s) Due dated Jan. 2, 2009 from U.S. Appl. No. 11/742,612 filed May 1, 2007.
U.S. Appl. No. 12/545,175 filed Aug. 21, 2009.

* cited by examiner

GLUCOPYRANOSYL-SUBSTITUTED (HETEROARYLOXY-BENZYL)-BENZENE DERIVATIVES, MEDICAMENTS CONTAINING SUCH COMPOUNDS, THEIR USE AND PROCESS FOR THEIR MANUFACTURE

RELATED CASES

This application claims priority benefit from EP 05008273 filed Apr. 15, 2005 and the the contents of which are incorporated herein.

THE INVENTION

The present invention relates to glucopyranosyl-substituted (heteroaryloxy-benzyl)-benzene derivatives of the general formula I

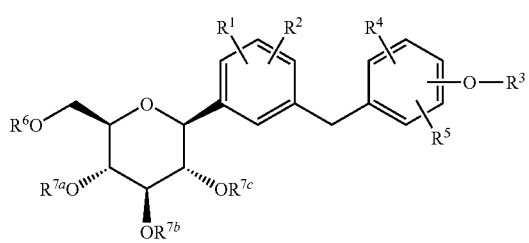

wherein the groups $R^1$ to $R^6$ and $R^{7a}$, $R^{7b}$, $R^{7c}$ are as defined hereinafter, including the tautomers, the stereoisomers, the mixtures thereof and the salts thereof. The invention further relates to pharmaceutical compositions containing a compound of formula I according to the invention as well as the use of a compound according to the invention for preparing a pharmaceutical composition for the treatment of metabolic disorders. In addition, the invention relates to processes for preparing a pharmaceutical composition as well as a compound according to the invention.

In the literature, compounds which have an inhibitory effect on the sodium-dependent glucose cotransporter SGLT2 are proposed for the treatment of diseases, particularly diabetes.

Glucopyranosyloxy-substituted aromatic groups and the preparation thereof and their possible activity as SGLT2 inhibitors are known from published International applications WO 98/31697, WO 01/27128, WO 02/083066, WO 03/099836, WO 2004/063209, WO 2004/080990, WO 2004/013118, WO 2004/052902, WO 2004/052903 and US application US 2003/0114390.

AIM OF THE INVENTION

The aim of the present invention is to find new pyranosyloxy-substituted benzene derivatives, particularly those which are active with regard to the sodium-dependent glucose cotransporter SGLT, particularly SGLT2. A further aim of the present invention is to discover pyranosyloxy-substituted benzene derivatives which have a good to very good inhibitory effect on the sodium-dependent glucose cotransporter SGLT2 in vitro and/or in vivo and/or have good to very good pharmacological and/or pharmacokinetic and/or physico-chemical properties.

A further aim of the present invention is to provide new pharmaceutical compositions which are suitable for the prevention and/or treatment of metabolic disorders, particularly diabetes.

The invention also sets out to provide a process for preparing the compounds according to the invention.

Other aims of the present invention will become apparent to the skilled man directly from the foregoing and following remarks.

OBJECT OF THE INVENTION

In a first aspect the present invention relates to glucopyranosyloxy-substituted (heteroaryloxy-benzyl)-benzene derivatives of general formula I

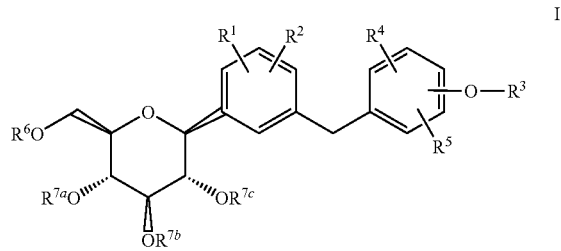

wherein $R^1$ denotes hydrogen, fluorine, chlorine, bromine, iodine, $C_{1-4}$-alkyl, $C_{2-6}$-alkynyl, $C_{1-4}$-alkoxy, $C_{2-4}$-alkenyl-$C_{1-4}$-alkoxy, $C_{2-4}$-alkynyl-$C_{1-4}$-alkoxy, methyl substituted by 1 to 3 fluorine atoms, ethyl substituted by 1 to 5 fluorine atoms, methoxy substituted by 1 to 3 fluorine atoms, ethoxy substituted by 1 to 5 fluorine atoms, $C_{1-4}$-alkyl substituted by a hydroxy or $C_{1-3}$-alkoxy group, $C_{2-4}$-alkoxy substituted by a hydroxy or $C_{1-3}$-alkoxy group, $C_{2-6}$-alkenyl, $C_{3-7}$-cycloalkyl, $C_{3-7}$-cycloalkyl-$C_{1-3}$-alkyl, $C_{3-7}$-cycloalkyloxy, $C_{3-7}$-cycloalkyl-$C_{1-3}$-alkoxy, $C_{5-7}$-cycloalkenyloxy, hydroxy, amino, nitro or cyano, while in the $C_{5-6}$-cycloalkyl groups a methylene group may be replaced by O;

$R^2$ denotes hydrogen, fluorine, chlorine, bromine, hydroxy, $C_{1-4}$-alkyl, $C_{1-4}$-alkoxy, cyano or nitro, while the alkyl or alkoxy group may be mono- or polysubstituted by fluorine, and $R^3$ denotes a 5- or 6-membered monocyclic heteroaryl-group which has 1 to 4 heteroatoms independently selected from the group consisting of N, O and S; or a 8-, 9- or 10-membered bicyclic heteroaryl-group which has 1 to 4 heteroatoms independently selected from the group consisting of N, O and S; and wherein the ring of the bicyclic heteroaryl-group attached to the ether oxygen of the group —O—$R^3$ is heteroaromatic; and wherein said heteroaryl-groups may possess 1 or 2 carbonyl groups as part of the mono- or bicyclic heteroaromatic ring-system; and wherein an N-atom of said heteroaryl-groups may be oxidized to form the corresponding N-oxide; and wherein one or more methine groups in said heteroaryl-groups may be substituted independently of one another with a substituent L1; and wherein one or more imino-groups in said heteroaryl-groups may be substituted independently of one another with a substituent $R^N$; and R⁴, R⁵ independently of one another denote hydrogen, fluorine, chlorine, bromine, iodine, cyano, nitro, $C_{1-3}$-alkyl, $C_{1-3}$-alkoxy, or a methyl- or methoxy-group substituted by 1 to 3 fluorine atoms, L1 independently of one another are selected from among fluorine, chlorine, bromine, iodine, hydroxy, cyano, $C_{1-3}$-alkyl, difluoromethyl, trifluoromethyl, $C_{1-3}$-alkoxy, difluoromethoxy, trifluoromethoxy, amino, $C_{1-3}$-alkyl-amino and di($C_{1-3}$-alkyl)-amino; and $R^N$ independently of one another are selected from among $C_{1-3}$-alkyl; and $R^6$, $R^{7a}$, $R^{7b}$, $R^{7c}$ independently of one another have a meaning selected from among hydrogen, ($C_{1-18}$-alkyl)carbonyl, ($C_{1-18}$-alkyl)oxycarbonyl, arylcarbonyl and aryl-($C_{1-3}$-alkyl)-carbonyl, while the aryl-groups may be mono- or disubstituted independently of one another by identical or different groups L1;

while by the aryl groups mentioned in the definition of the above groups are meant phenyl or naphthyl groups which may be substituted as defined; and while, unless otherwise stated, the above-mentioned alkyl groups may be straight or branched chain, the tautomers, the stereoisomers thereof, the mixtures thereof and the salts thereof.

The compounds of general formula I according to the invention and the physiologically acceptable salts thereof have valuable pharmacological properties, particularly an inhibitory effect on the sodium-dependent glucose cotransporter SGLT, particularly SGLT2. Moreover compounds according to the invention may have an inhibitory effect on the sodium-dependent glucose cotransporter SGLT1. Compared with a possible inhibitory effect on SGLT1 the compounds according to the invention preferably inhibit SGLT2 selectively. Furthermore the compounds according to this invention exhibit advantageous physicochemical properties, particularly a good tendency towards crystallization.

The present invention also relates to the physiologically acceptable salts of the compounds according to the invention with inorganic or organic acids.

This invention also relates to pharmaceutical compositions, containing at least one compound according to the invention or a physiologically acceptable salt according to the invention, optionally together with one or more inert carriers and/or diluents.

This invention also relates to the use of at least one compound according to the invention or one of the physiologically acceptable salts thereof for preparing a pharmaceutical composition which is suitable for the treatment or prevention or diseases or conditions which can be influenced by inhibiting the sodium-dependent glucose cotransporter SGLT, particularly SGLT2.

This invention also relates to the use of at least one compound according to the invention or one of the physiologically acceptable salts thereof for preparing a pharmaceutical composition which is suitable for the treatment of metabolic disorders.

This invention also relates to the use of at least one compound according to the invention or one of the physiologically acceptable salts thereof for preparing a pharmaceutical composition for inhibiting the sodium-dependent glucose cotransporter SGLT, particularly SGLT2.

The invention further relates to a process for preparing a pharmaceutical composition according to the invention, characterised in that a compound according to the invention or one of the physiologically acceptable salts thereof is incorporated in one or more inert carriers and/or diluents by a non-chemical method.

The present invention also relates to a process for preparing the compounds of general formula I according to the invention, characterised in that a) in order to prepare compounds of general formula I which are defined as hereinbefore and hereinafter, a compound of general formula I

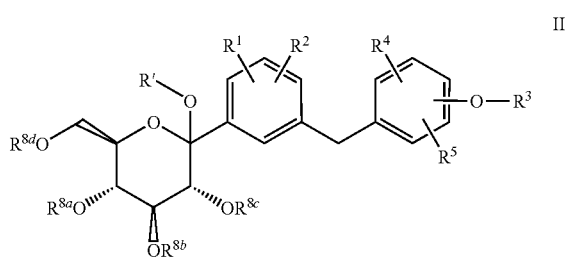

II wherein

R' denotes H, $C_{1-4}$-alkyl, ($C_{1-18}$-alkyl)carbonyl, ($C_{1-18}$-alkyl)oxycarbonyl, arylcarbonyl and aryl-($C_{1-3}$-alkyl)-carbonyl, wherein the alkyl or aryl groups may be mono- or polysubstituted by halogen;

$R^{8a}$, $R^{8b}$, $R^{8c}$, $R^{8d}$ independently of one another have one of the meanings given hereinbefore and hereinafter for the groups $R^6$, $R^{7a}$, $R^{7b}$, $R^{7c}$, denote a benzyl group or a $R^aR^bR^cSi$ group or a ketal or acetal group, particularly an alkylidene or arylalkylidene ketal or acetal group, while in each case two adjacent groups $R^{8a}$, $R^{8b}$, $R^{8c}$, $R^{8d}$ may form a cyclic ketal or acetal group or a 1,2-di($C_{1-3}$-alkoxy)-1,2-di($C_{1-3}$-alkyl)ethylene bridge, while the above-mentioned ethylene bridge forms, together with two oxygen atoms and the two associated carbon atoms of the pyranose ring, a substituted dioxane ring, particularly a 2,3-dimethyl-2,3-di($C_{1-3}$-alkoxy)-1,4-dioxane ring, and while alkyl, aryl and/or benzyl groups may be mono- or polysubstituted by halogen or $C_{1-3}$-alkoxy, and while benzyl groups may also be substituted by a di-($C_{1-3}$-alkyl)amino group; and $R^a$, $R^b$, $R^c$ independently of one another denote $C_{1-4}$-alkyl, aryl or aryl-$C_{1-3}$-alkyl, wherein the aryl or alkyl groups may be mono- or polysubstituted by halogen;

while by the aryl groups mentioned in the definition of the above groups are meant phenyl or naphthyl groups, preferably phenyl groups;

and wherein the groups $R^1$ to $R^5$ and $R^6$, $R^{7a}$, $R^{7b}$, $R^{7c}$ are defined as hereinbefore and hereinafter;

is reacted with a reducing agent in the presence of a Lewis or Brønsted acid, while any protective groups present are cleaved simultaneously or subsequently; or b) in order to prepare compounds of general formula I wherein $R^6$, $R^{7a}$, $R^{7b}$ and $R^{7c}$ denote hydrogen, a compound of general formula III

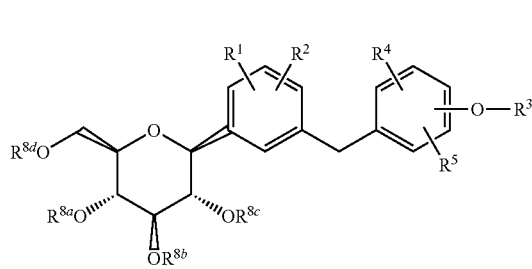

wherein $R^{8a}$, $R^{8b}$, $R^{8c}$, $R^{8d}$ and $R^1$ to $R^5$ are defined as hereinbefore and hereinafter, but at least one of the groups $R^{8a}$, $R^{8b}$, $R^{8c}$, $R^{8d}$ does not denote hydrogen, is hydrolysed, and if desired a compound of general formula I thus obtained wherein $R^6$ denotes a hydrogen atom, is converted by acylation into a corresponding acyl compound of general formula I, and/or if necessary any protective group used in the reactions described above is cleaved and/or if desired a compound of general formula I thus obtained is resolved into its stereoisomers and/or if desired a compound of general formula I thus obtained is converted into the salts thereof, particularly for pharmaceutical use into the physiologically acceptable salts thereof.

This invention further relates to a process for preparing compounds of general formula II

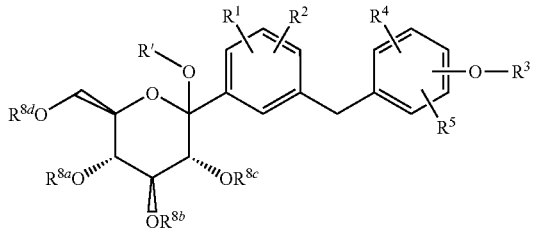

wherein
R' denotes H, $C_{1-4}$-alkyl, $(C_{1-18}$-alkyl)carbonyl, $(C_{1-18}$-alkyl)oxycarbonyl, arylcarbonyl and aryl-$(C_{1-3}$-alkyl)-carbonyl, wherein the alkyl or aryl groups may be mono- or polysubstituted by halogen;
$R^{8a}$, $R^{8b}$, $R^{8c}$, $R^{8d}$ independently of one another has one of the meanings given for the groups $R^5$, $R^{7a}$, $R^{7b}$, $R^{7c}$, denote a benzyl group or a $R^a R^b R^c Si$ group or a ketal or acetal group, while in each case two adjacent groups $R^{8a}$, $R^{8b}$, $R^{8c}$, $R^{8d}$ may form a cyclic ketal or acetal group or may form, with two oxygen atoms of the pyranose ring, a substituted 2,3-oxydioxane ring, particularly a 2,3-dimethyl-2,3-di($C_{1-3}$-alkoxy)-1,4-dioxane ring, and while alkyl, aryl and/or benzyl groups may be mono- or polysubstituted by halogen or $C_{1-3}$-alkoxy, and while benzyl groups may also be substituted by a di-$(C_{1-3}$-alkyl)amino group; and
$R^a$, $R^b$, $R^c$ independently of one another denote $C_{1-4}$-alkyl, aryl or aryl-$C_{1-3}$-alkyl, while the alkyl or aryl groups may be mono- or polysubstituted by halogen;

while by the aryl groups mentioned in the definition of the above groups are meant phenyl or naphthyl groups, preferably phenyl groups;

and $R^1$ to $R^5$, $R^6$, $R^{7a}$, $R^{7b}$, $R^{7c}$ are defined as hereinbefore and hereinafter, wherein an organometallic compound (V) which may be obtained by halogen-metal exchange or by inserting a metal in the carbon-halogen bond of a halogen-benzylbenzene compound of general formula IV

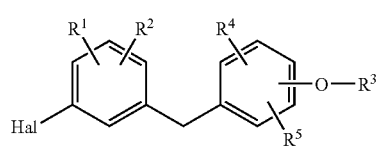

wherein Hal denotes Cl, Br and I and $R^1$ to $R^5$ are defined as hereinbefore and hereinafter, and optionally subsequent transmetallation, is added to a gluconolactone of general formula VI

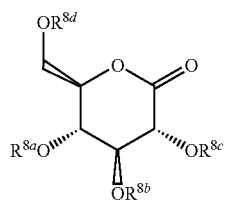

wherein $R^{8a}$, $R^{8b}$, $R^{8c}$, $R^{8d}$ are defined as hereinbefore and hereinafter, and then the resulting adduct, is reacted, preferably in situ, with water or an alcohol R'—OH, while R' denotes optionally substituted $C_{1-4}$-alkyl, in the presence of an acid, such as for example methanesulphonic acid, sulphuric acid, hydrochloric acid, acetic acid or ammonium chloride, and optionally the product obtained in the reaction with water wherein R' denotes H is converted, in a subsequent reaction, with an acylating agent, such as for example the corresponding acid chloride or anhydride, into the product of formula II wherein R' denotes $(C_{1-18}$-alkyl)carbonyl, $(C_{1-18}$-alkyl)oxycarbonyl, arylcarbonyl or aryl-$(C_{1-3}$-alkyl)-carbonyl, which may be substituted as specified.

The intermediate products listed, particularly those of formula IV, formula II and formula III, are also a subject of this invention.

DETAILED DESCRIPTION OF THE INVENTION

Unless otherwise stated, the groups, residues and substituents, particularly $R^1$ to $R^5$, L1, $R^N$, $R^6$, $R^{7a}$, $R^{7b}$, $R^{7c}$, $R^{8a}$, $R^{8b}$, $R^{8c}$, $R^{8d}$, are defined as above and hereinafter.

If residues, substituents or groups occur several times in a compound, as for example L1 and/or $R^N$, they may have the same or different meanings.

Some preferred meanings of individual groups and substituents of the compounds according to the invention will be given hereinafter.

The group —O—R³ is preferably in the meta or para position to the —CH₂-bridge, so that compounds according to the following formulae I.1 and I.2, particularly formula I.2, are preferred:

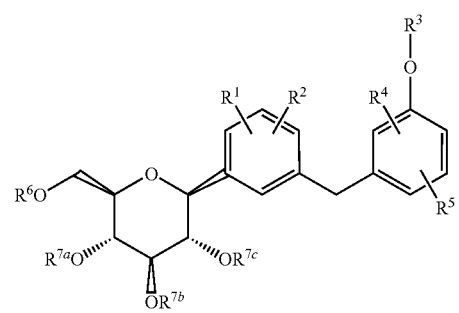

I.1

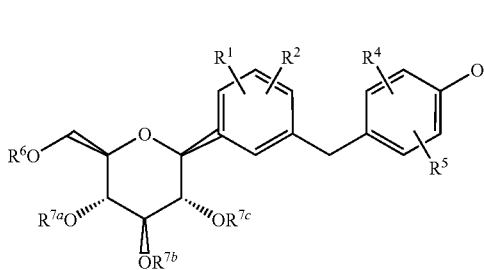

I.2

The group $R^1$ preferably denotes hydrogen, fluorine, chlorine, bromine, $C_{1-4}$-alkyl, $C_{1-4}$-alkoxy, methyl substituted by 1 to 3 fluorine atoms, methoxy substituted by 1 to 3 fluorine atoms, $C_{3-7}$-cycloalkyloxy or $C_{3-7}$-cycloalkyl-$C_{1-3}$-alkoxy, while in the $C_{5-6}$-cycloalkyl groups a methylene group may be replaced by O.

Particularly preferred meanings of $R^1$ are hydrogen, fluorine, chlorine, methyl, methoxy, ethoxy, cyclopentyloxy, cyclohexyloxy, tetrahydrofuran-3-yloxy and tetrahydropyran-4-yl-oxy; particularly methyl and chlorine.

Preferred meanings of the group $R^2$ are hydrogen, fluorine, chlorine, methyl, methoxy, ethoxy and methyl substituted by 1 to 3 fluorine atoms.

Particularly preferred meanings of the group $R^2$ are hydrogen, fluorine, methoxy, ethoxy and methyl, particularly hydrogen.

The term 5- or 6-membered monocyclic heteroaryl-group as used in the definition of the group $R^3$ preferably denotes a pyrrolyl, furanyl, thienyl, pyridyl or tetrazolyl group, or a pyrrolyl, furanyl, thienyl or pyridyl group wherein one or two methine groups are replaced in each case by a nitrogen atom, wherein said heteroaryl-groups may possess 1 or 2 carbonyl groups as part of the heteroaromatic ring-system;

wherein an N-atom of the heteroaryl ring-system may be oxidized to form the corresponding N-oxide; and wherein one or more methine-groups may be substituted independently of one another with a substituent L1; and wherein one or more imino-groups may be substituted independently of one another with a substituent $R^N$.

The term 8-, 9- or 10-membered bicyclic heteroaryl-group as used in the definition of the group $R^3$ preferably denotes a indolyl, benzofuranyl, benzothiophenyl, quinolinyl or isoquinolinyl group, or an indolyl, benzofuranyl, benzothiophenyl, quinolinyl or isoquinolinyl group wherein one to three methine groups are replaced in each case by a nitrogen atom, wherein the ring of the bicyclic heteroaryl-group attached to the ether oxygen of the group —O—R³ is heteroaromatic; and wherein said heteroaryl-groups may possess 1 or 2 carbonyl groups as part of the aromatic ring-system;

wherein an N-atom of the heteroaryl ring-system may be oxidized to form the corresponding N-oxide; and wherein one or more methine-groups may be substituted independently of one another with a substituent L1; and wherein one or more imino-groups may be substituted independently of one another with a substituent $R^N$.

In heteroaryl-groups which possess 1 or 2 carbonyl groups as part of the aromatic ring-system each carbonyl group is preferably directly linked with an optionally substituted imino-group —NH—, thus forming a —NH—CO— group, or linked with an optionally substituted imino-group —NH— via an ethenylene-bridge, thus forming a —NH—CH═CH—CO— group.

Preferably the group $R^3$ denotes an optionally substituted 5- or 6-membered monocyclic heteroaryl-group as defined above.

More preferably the group $R^3$ denotes pyridyl, pyridazinyl, pyrazinyl, pyrimidinyl, triazinyl, N-oxy-pyridyl, N-oxy-pyridazinyl, N-oxy-pyrazinyl, N-oxy-pyrimidinyl, pyrazolyl, imidazolyl, furanyl, thienyl, thiazolyl, oxazolyl, isoxazolyl, oxadiazolyl, triazolyl, tetrazolyl, 1,2-dihydro-2-oxo-pyridinyl, 1,4-dihydro-4-oxo-pyridinyl, 2,3-dihydro-3-oxo-pyridazinyl, 1,2,3,6-tetrahydro-3,6-dioxo-pyridazinyl, 1,2-dihydro-2-oxo-pyrimidinyl, 3,4-dihydro-4-oxo-pyrimidinyl, 1,2,3,4-tetrahydro-2,4-dioxo-pyrimidinyl, 1,2-dihydro-2-oxo-pyrazinyl or 1,2,3,4-tetrahydro-2,3-dioxo-pyrazinyl, wherein one or more methine-groups in said heteroaryl-groups may be substituted independently of one another with a substituent L1; and wherein one or more imino-groups in said heteroaryl-groups may be substituted independently of one another with a substituent $R^N$.

Even more preferably the group $R^3$ denotes pyridyl, pyridazinyl, pyrazinyl, pyrimidinyl, pyrazolyl, imidazolyl, triazinyl, thienyl, thiazolyl, oxazolyl, isoxazolyl, [1,2,4]oxadiazolyl, 1H-[1,2,4]triazolyl, or 2H-tetrazolyl, wherein one or more methine-groups in said heteroaryl-groups may be substituted independently of one another with a substituent L1; and wherein one or more imino-groups in said heteroaryl-groups may be substituted independently of one another with a substituent $R^N$.

Most preferably the group $R^3$ is selected from the subformulas depicted in Table A,

TABLE A

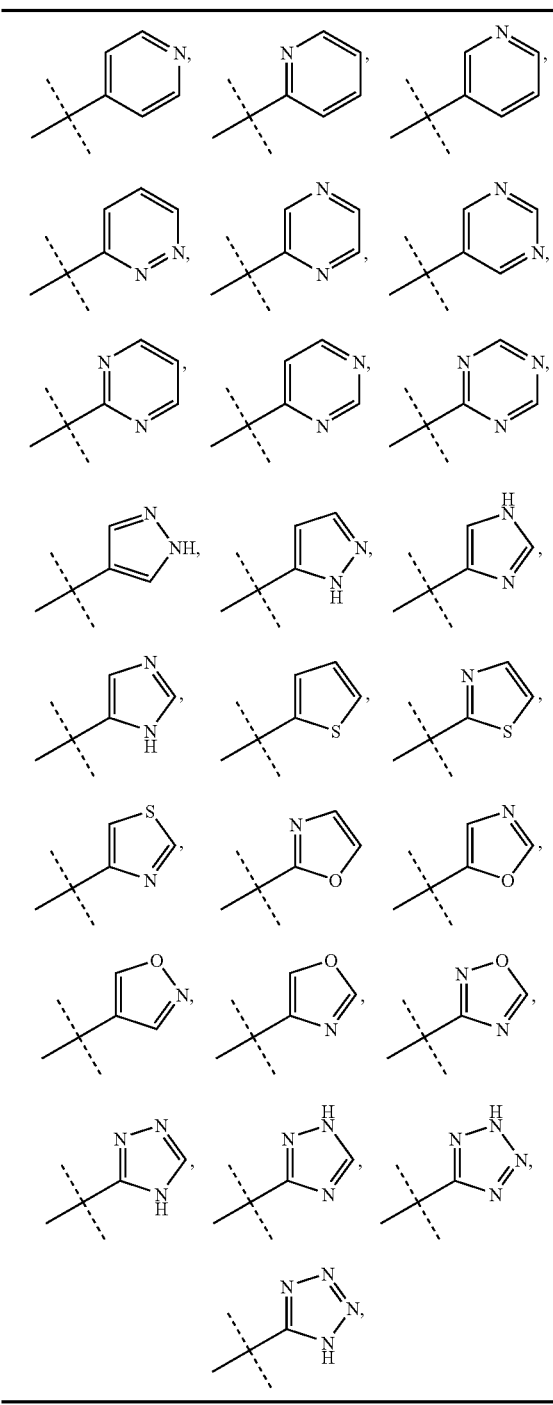

wherein, as described before, all tautomeric forms are included; and wherein one or more methine-groups may be substituted independently of one another with a substituent L1; preferably wherein the methine groups are unsubstituted or one or two methine-groups are substituted independently of one another with L1; and wherein one or more imino-groups may be substituted independently of one another with a substituent $R^N$.

Preferred meanings of the group L1 independently of one another are selected from among fluorine, chlorine, bromine, cyano, hydroxy, $C_{1-3}$-alkyl, difluoromethyl, trifluoromethyl, $C_{1-3}$-alkoxy, difluoromethoxy, trifluoromethoxy and di($C_{1-3}$-alkyl)-amino.

Particularly preferred meanings of the group L1 are selected from fluorine, chlorine, hydroxy, methyl, trifluoromethyl, ethyl, methoxy, ethoxy and dimethylamino, particularly methyl, ethyl, methoxy, ethoxy and dimethylamino.

Preferred meanings of the group $R^N$ independently of one another are selected from among methyl, ethyl, n-propyl and i-propyl; most preferably methyl and ethyl.

Preferred meanings of the group $R^4$ are hydrogen and fluorine, particularly hydrogen.

Preferred meanings of the group $R^5$ are hydrogen and fluorine, particularly hydrogen.

The group $R^6$ preferably denotes according to the invention hydrogen, ($C_{1-8}$-alkyl)oxycarbonyl, $C_{1-8}$-alkylcarbonyl or benzoyl, particularly hydrogen or ($C_{1-6}$-alkyl)oxycarbonyl or $C_{1-6}$-alkylcarbonyl, particularly preferably hydrogen, methylcarbonyl, methoxycarbonyl or ethoxycarbonyl, most particularly preferably hydrogen.

The substituents $R^{7a}$, $R^{7b}$, $R^{7c}$ preferably represent independently of one another hydrogen, ($C_{1-8}$-alkyl)oxycarbonyl, ($C_{1-18}$-alkyl)carbonyl or benzoyl, particularly hydrogen, ($C_{1-6}$-alkyl) oxycarbonyl or ($C_{1-8}$-alkyl)carbonyl, particularly preferably hydrogen, methoxycarbonyl, ethoxycarbonyl, methylcarbonyl or ethylcarbonyl. Most particularly preferably $R^{7a}$, $R^{7b}$ and $R^{7c}$ represent hydrogen.

The compounds of formula I wherein $R^6$, $R^{7a}$, $R^{7b}$ and $R^{7c}$ according to the invention have a meaning other than hydrogen, for example $C_{1-8}$-alkylcarbonyl, are preferably suitable as intermediate products for the synthesis of compounds of formula I wherein $R^6$, $R^{7a}$, $R^{7b}$ and $R^{7c}$ denote hydrogen.

Particularly preferred compounds of general formula I are selected from among formulae I.2a to I.2d, particularly I.2c:

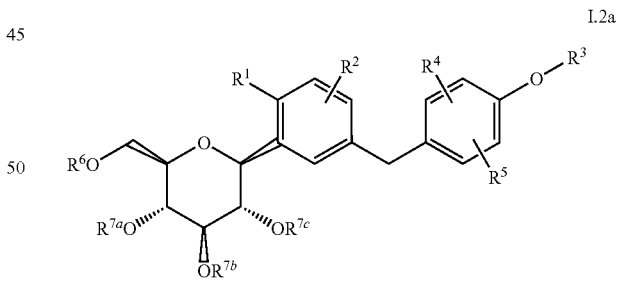

I.2a

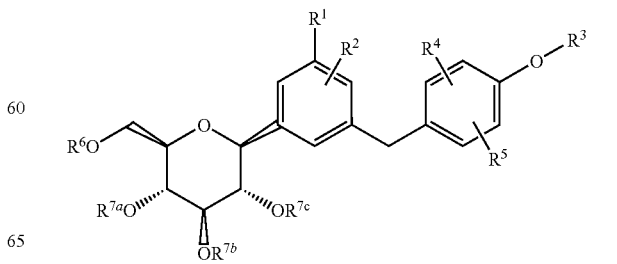

I.2b

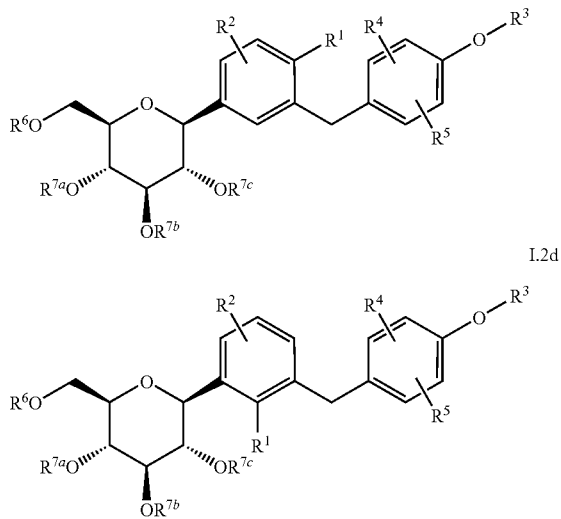

while the groups $R^1$ to $R^6$ and $R^{7a}$, $R^{7b}$, $R^{7c}$ have one of the meanings given previously, particularly have one of the given meanings specified as being preferred; and particularly $R^1$ denotes hydrogen, fluorine, chlorine, bromine, $C_{1-4}$-alkyl, $C_{1-4}$-alkoxy, methyl substituted by 1 to 3 fluorine atoms, methoxy substituted by 1 to 3 fluorine atoms, $C_{3-7}$-cycloalkyloxy or $C_{3-7}$-cycloalkyl-$C_{1-3}$-alkoxy, while in the $C_{5-6}$-cycloalkyl groups a methylene group may be replaced by O; $R^1$ particularly preferably denotes hydrogen, fluorine, chlorine, methyl, methoxy, ethoxy, cyclopentyloxy, cyclohexyloxy, tetrahydrofuran-3-yloxy or tetrahydropyran-4-yl-oxy; and $R^2$ denotes hydrogen, fluorine, methoxy, ethoxy or methyl, particularly hydrogen; and $R^3$ is selected from the group consisting of pyridyl, pyridazinyl, pyrazinyl, pyrimidinyl, pyrazolyl, imidazolyl, triazinyl, furanyl, thienyl, thiazolyl, oxazolyl, isoxazolyl, oxadiazolyl, triazolyl, and tetrazolyl; particularly selected from the subformulas as depicted in the above Table A;

wherein one or more methine-groups may be substituted independently of one another with a substituent L1; and wherein one or more imino-groups may be substituted independently of one another with a substituent $R^N$; and $R^4$ denotes hydrogen or fluorine, particularly hydrogen; and $R^5$ denotes hydrogen or fluorine, particularly hydrogen; and L1 independently of one another are selected from among fluorine, chlorine, bromine, cyano, hydroxy, $C_{1-3}$-alkyl, difluoromethyl, trifluoromethyl, $C_{1-3}$-alkoxy, difluoromethoxy, trifluoromethoxy and di($C_{1-3}$-alkyl)-amino; particularly selected from among fluorine, chlorine, hydroxy, methyl, trifluoromethyl, ethyl, methoxy, ethoxy and dimethylamino; most preferably selected from among methyl, ethyl, methoxy, ethoxy and dimethylamino; and;

$R^N$ independently of one another are selected from among $C_{1-3}$-alkyl; in particular methyl and ethyl; and $R^6$ denotes hydrogen, ($C_{1-6}$-alkyl)oxycarbonyl, ($C_{1-6}$-alkyl)carbonyl or benzoyl, particularly hydrogen, methylcarbonyl, methoxycarbonyl or ethoxycarbonyl, most particularly preferably hydrogen; and $R^{7a}$, $R^{7b}$, $R^{7c}$ independently of one another represent hydrogen, ($C_{1-6}$-alkyl)oxycarbonyl, ($C_{1-8}$-alkyl)carbonyl or benzoyl, particularly hydrogen, methoxycarbonyl, ethoxycarbonyl, methylcarbonyl or ethylcarbonyl, particularly preferably hydrogen;

including the tautomers, the stereoisomers, the mixtures thereof and the salts thereof.

According to a variant of the embodiments given hereinbefore, other preferred compounds are those wherein the phenyl group which carries the substituent —O—$R^3$ has at least one other substituent $R^4$ and/or $R^5$ which is different from hydrogen. According to this variant, particularly preferred compounds are those which have a substituent $R^4$ representing fluorine.

The compounds of general formula I specified in the experimental section that follows, and the derivatives thereof, wherein $R^6$ has a meaning according to the invention other than hydrogen, particularly wherein $R^6$ denotes ethoxycarbonyl or methoxycarbonyl, including the tautomers, the stereoisomers thereof and the mixtures thereof, are preferred according to another variant of this invention.

In the processes according to the invention the groups $R^1$, $R^2$, $R^3$, $R^4$ and $R^5$ preferably have the meanings specified hereinbefore as being preferred. Moreover R' preferably denotes H, $C_{1-3}$-alkyl or benzyl, particularly H, ethyl or methyl. The groups $R^{8a}$, $R^{8b}$, $R^{8c}$ and $R^{8d}$ independently of one another preferably denote H, $C_{1-4}$-alkylcarbonyl or benzyl, particularly H, methylcarbonyl, ethylcarbonyl or benzyl.

The invention also relates to compounds of general formula IV, particularly of general formula IV'

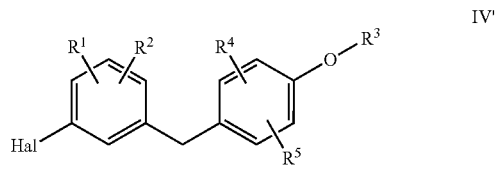

wherein Hal denotes chlorine, bromine or iodine and the groups $R^1$, $R^2$, $R^3$, $R^4$ and $R^5$ are as hereinbefore defined, as intermediate products or starting materials in the synthesis of the compounds according to the invention. Particularly preferably, the groups $R^1$, $R^2$, $R^3$, $R^4$ and $R^5$ have the meanings given following formulae I.2a to I.2d.

The invention also relates to compounds of general formula II, particularly of general formula II'

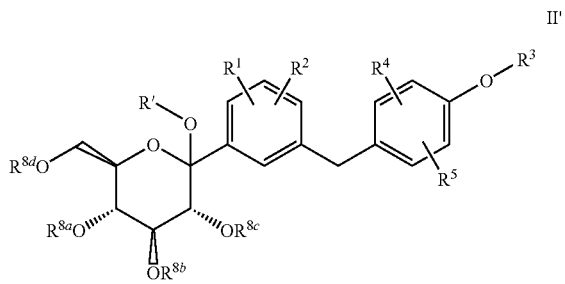

wherein R', $R^{8a}$, $R^{8b}$, $R^{8c}$, $R^{8d}$, $R^1$, $R^2$ $R^3$ $R^4$ and $R^5$ are defined as hereinbefore and hereinafter; particularly wherein R' denotes H, $C_{1-3}$-alkyl or benzyl, particularly H, ethyl or methyl; and the groups $R^{8a}$, $R^{8b}$, $R^{8c}$ and $R^{8d}$ independently of one another represent H, $C_{1-4}$-alkylcarbonyl or benzyl, particularly H, methylcarbonyl, ethylcarbonyl or benzyl and the groups $R^1$, $R^2$, $R^3$, $R^4$ and $R^5$ are as hereinbefore defined, as intermediate products or starting materials in the synthesis of the compounds according to the invention. Particularly preferably the groups $R^1$, $R^2$, $R^3$, $R^4$ and $R^5$ have the meanings given following formulae I.2a to I.2d.

Some terms used above and hereinafter to describe the compounds according to the invention will now be defined more closely.

The term halogen denotes an atom selected from the group consisting of F, Cl, Br and I, particularly F, Cl and Br.

The term $C_{1-n}$-alkyl, wherein n may have a value of 1 to 18, denotes a saturated, branched or unbranched hydrocarbon group with 1 to n C atoms. Examples of such groups include methyl, ethyl, n-propyl, iso-propyl, butyl, iso-butyl, sec-butyl, tert-butyl, n-pentyl, iso-pentyl, neo-pentyl, tert-pentyl, n-hexyl, iso-hexyl, etc.

The term $C_{2-n}$-alkynyl, wherein n has a value of 3 to 6, denotes a branched or unbranched hydrocarbon group with 2 to n C atoms and a C≡C triple bond. Examples of such groups include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl etc. Unless otherwise stated alkynyl groups are connected to the remainder of the molecule via the C atom in position 1. Therefore terms such as 1-propynyl, 2-propynyl, 1-butynyl, etc. are equivalent to the terms 1-propyn-1-yl, 2-propyn-1-yl, 1-butyn-1-yl, etc. This also applies analogously to $C_{2-n}$-alkenyl groups.

The term $C_{1-n}$-alkoxy denotes a $C_{1-n}$-alkyl-O group, wherein $C_{1-n}$-alkyl is as hereinbefore defined. Examples of such groups include methoxy, ethoxy, n-propoxy, iso-propoxy, n-butoxy, iso-butoxy, sec-butoxy, tert-butoxy, n-pentoxy, iso-pentoxy, neo-pentoxy, tert-pentoxy, n-hexoxy, iso-hexoxy etc.

The term $C_{1-n}$-alkylcarbonyl denotes a $C_{1-n}$-alkyl-C(=O) group, wherein $C_{1-n}$-alkyl is as hereinbefore defined. Examples of such groups include methylcarbonyl, ethylcarbonyl, n-propylcarbonyl, iso-propylcarbonyl, n-butylcarbonyl, iso-butylcarbonyl, sec-butylcarbonyl, tert-butylcarbonyl, n-pentylcarbonyl, iso-pentylcarbonyl, neo-pentylcarbonyl, tert-pentylcarbonyl, n-hexylcarbonyl, iso-hexylcarbonyl, etc.

The term $C_{3-n}$-cycloalkyl denotes a saturated mono-, bi-, tri- or spirocarbocyclic group with 3 to n C atoms. Examples of such groups include cyclopropyl, cyclobutyl, cyclopentyl, cyclohexyl, cycloheptyl, cyclooctyl, cyclononyl, cyclododecyl, bicyclo[3.2.1.]octyl, spiro[4.5]decyl, norpinyl, norbonyl, norcaryl, adamantyl, etc. Preferably the term $C_{3-7}$-cycloalkyl denotes saturated monocyclic groups.

The term $C_{5-n}$-cycloalkenyl denotes a $C_{5-n}$-cycloalkyl group which is as hereinbefore defined and additionally has at least one unsaturated C=C double bond.

The term $C_{3-n}$-cycloalkylcarbonyl denotes a $C_{3-n}$-cycloalkyl-C(=O) group wherein $C_{3-n}$-cycloalkyl is as hereinbefore defined.

The term tri-($C_{1-4}$-alkyl)silyl comprises silyl groups which have identical or two or three different alkyl groups.

The term di-($C_{1-3}$-alkyl)amino comprises amino groups which have identical or two different alkyl groups.

The term aryl preferably denotes naphthyl or phenyl, more preferably phenyl.

The nomenclature in structural formulas used above and hereinafter, in which a bond of a substituent of a cyclic group, as e.g. a phenyl ring, is shown towards the centre of the cyclic group, denotes, unless otherwise stated, that this substituent may be bound to any free position of the cyclic group bearing an H atom.

The compounds according to the invention may be obtained using methods of synthesis known in principle. Preferably the compounds are obtained by the following methods according to the invention which are described in more detail hereinafter.

The glucose derivatives of formula II according to the invention may be synthesised from D-gluconolactone or a derivative thereof by adding the desired benzylbenzene compound in the form of an organometallic compound (Scheme 1).

Scheme 1: Addition of an Organometal Compound to a Gluconolactone

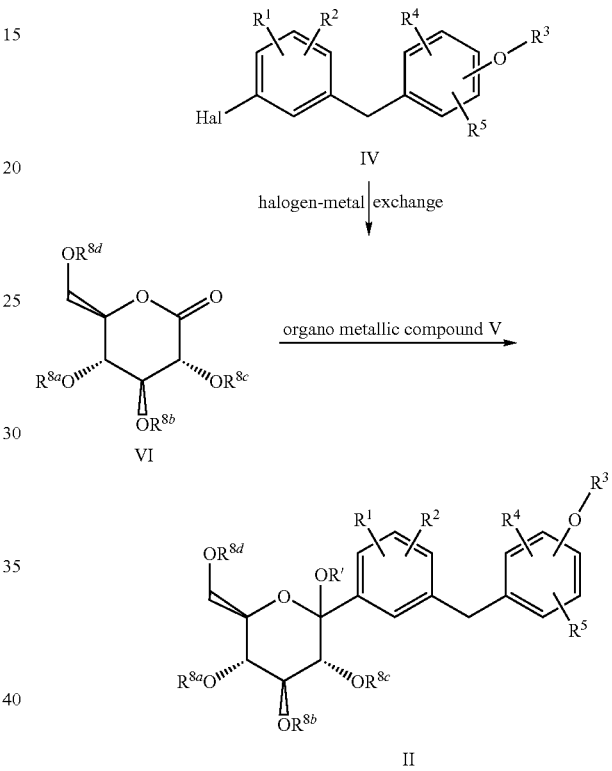

The reaction according to Scheme 1 is preferably carried out starting from a halogenated benzylbenzene compound of general formula IV, wherein Hal denotes chlorine, bromine, or iodine. Starting from the haloaromatic compound IV the corresponding organometallic compound (V) may be prepared either by means of a so-called halogen-metal exchange reaction or by inserting the metal into the carbon-halogen bond. The halogen-metal exchange with bromine or iodine-substituted aromatic groups may be carried out for example with an organolithium compound such as e.g. n-, sec- or tert-butyllithium and thereby yields the corresponding lithiated aromatic group. The analogous magnesium compound may also be generated by a halogen-metal exchange with a suitable Grignard reagent such as e.g. isopropylmagnesium bromide or diisopropylmagnesium. The reactions are preferably carried out between 0 and −100° C., particularly preferably between −10 and −80° C., in an inert solvent or mixtures thereof, such as for example diethyl ether, tetrahydrofuran, toluene, hexane, or methylene chloride. The magnesium or lithium compounds thus obtained may optionally be transmetallated with metal salts such as e.g. cerium trichloride, to form alternative organometal compounds (V) suitable for addition. Alternatively, the organometallic compound (V)

may also be prepared by inserting a metal into the carbon-halogen bond of the haloaromatic compound IV. Metals such as e.g. lithium or magnesium are suitable for this. The addition of the organometallic compound V to gluconolactone or derivatives thereof of formula VI is preferably carried out at temperatures between 0 and −100° C., particularly preferably at −30 to −80° C., in an inert solvent or mixtures thereof, to obtain the compound of formula II. The lithiation and/or coupling reaction may also be carried out in microreactors and/or micromixers in order to avoid low temperatures; for example analogously to the processes described in WO 2004/076470. Suitable solvents for the addition of the metallated phenyl group to the appropriately protected gluconolactone are e.g. diethyl ether, toluene, methylene chloride, hexane, tetrahydrofuran or mixtures thereof. The addition reactions may be carried out without any further adjuvants or in the case of sluggishly reacting coupling partners in the presence of Lewis acids such as e.g. $BF_3*OEt_2$ or $Me_3SiCl$ (see M. Schlosser, Organometallics in Synthesis, John Wiley & Sons, Chichester/New York/Brisbane/Toronto/Singapore, 1994). Preferred definitions of the groups $R^{8a}$, $R^{8b}$, $R^{8c}$ and $R^{8d}$ are benzyl, substituted benzyl, trialkylsilyl, particularly preferably trimethylsilyl, triisopropylsilyl, 4-methoxybenzyl and benzyl. If two adjacent groups of the group consisting of $R^{8a}$, $R^{8b}$, $R^{8c}$ and $R^{8d}$ are linked together, these two groups are preferably part of a benzylideneacetal, 4-methoxybenzylideneacetal, isopropylketal or constitute a 2,3-dimethoxy-butylene group which is linked via the 2 and 3 positions of the butane with the adjacent oxygen atoms of the pyranose ring. The group R' preferably denotes hydrogen or $C_{1-4}$-alkyl, particularly preferably hydrogen, methyl or ethyl. The group R' is inserted after the addition of the organometallic compound V or a derivative thereof to the gluconolactone VI. For this purpose the reaction solution is treated with an alcohol such as e.g. methanol or ethanol or water in the presence of an acid such as e.g. methanesulphonic acid, toluenesulphonic acid, sulphuric acid, or hydrochloric acid.

The synthesis of haloaromatic compounds of formula IV may be carried out using standard transformations in organic chemistry or at least methods known from the specialist literature in organic synthesis (see inter alia J. March, Advanced Organic Reactions, Reactions, Mechanisms, and Structure, 4th Edition, John Wiley & Sons, Chichester/New York/Brisbane/Toronto/Singapore, 1992 and literature cited therein). Residue $R^3$ as defined herein may be introduced before, as presented above, or after the glucose moiety has been attached to the aglycon part. In principle, $R^3$ can be appended at any stage of the entire reaction sequence. The preferred stage of attachment, as presented above, is before the glucose part has been incorporated.

In order to prepare compounds of general formula I, in process a) according to the invention, a compound of general formula II

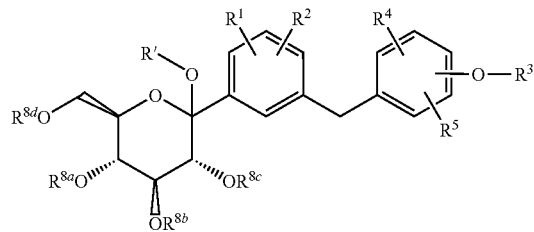

wherein R', $R^1$ to $R^5$ are as hereinbefore defined and $R^{8a}$, $R^{8b}$, $R^{8c}$, $R^{8d}$ are as hereinbefore defined and independently of one another represent for example acetyl, pivaloyl, benzoyl, tert-butoxycarbonyl, benzyloxycarbonyl, trialkylsilyl, benzyl or substituted benzyl or in each case two adjacent groups $R^{8a}$, $R^{8b}$, $R^{8c}$, $R^{8d}$ form a benzylideneacetal or isopropylideneketal or a 2,3-dimethoxy-butylene group which is linked via position 2 and 3 of the butylene group to the oxygen atoms of the pyranose ring and forms with them a substituted dioxane, which may be obtained as hereinbefore described, is reacted with a reducing agent in the presence of a Lewis or Brønsted acid.

Suitable reducing agents for the reaction include for example silanes, such as triethyl, tripropyl, triisopropyl or diphenylsilane, sodium borohydride, sodium cyanoborohydride, zinc borohydride, boranes, lithium aluminium hydride, diisobutylaluminium hydride or samarium iodide. The reductions are carried out without or in the presence of a suitable Brønsted acid, such as e.g. hydrochloric acid, toluenesulphonic acid, trifluoroacetic acid or acetic acid, or Lewis acid, such as e.g. boron trifluoride etherate, trimethylsilyltriflate, titaniium tetrachloride, tin tetrachloride, scandium triflate or zinc iodide. Depending on the reducing agent and the acid the reaction may be carried out in a solvent, such as for example methylene chloride, chloroform, acetonitrile, toluene, hexane, diethyl ether, tetrahydrofuran, dioxane, ethanol, water or mixtures thereof at temperatures between −60° C. and 120° C. One particularly suitable combination of reagents consists for example of triethylsilane and boron trifluoride etherate, which is conveniently used in acetonitrile or dichloromethane at temperatures of −60° C. and 60° C. Moreover, hydrogen may be used in the presence of a transition metal catalyst, such as e.g. palladium on charcoal or Raney nickel, in solvents such as tetrahydrofuran, ethyl acetate, methanol, ethanol, water or acetic acid, for the transformation described.

Alternatively, in order to prepare compounds of general formula I according to process b) according to the invention, in a compound of general formula III

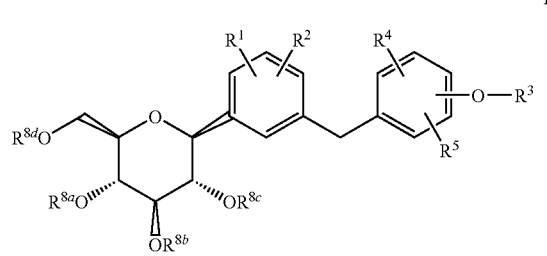

wherein $R^1$ to $R^5$ are as hereinbefore defined and $R^{8a}$ to $R^{8d}$ denote one of the protective groups defined hereinbefore, such as e.g. an acyl, arylmethyl, acetal, ketal or silyl group, and which may be obtained for example by reduction from the compound of formula II as hereinbefore described, the protective groups are cleaved.

Any acyl protecting group used is cleaved for example hydrolytically in an aqueous solvent, e.g. in water, isopropanol/water, acetic acid/water, tetrahydrofuran/water or dioxane/water, in the presence of an acid such as trifluoroacetic acid, hydrochloric acid or sulphuric acid or in the presence of an alkali metal base such as lithium hydroxide, sodium hydroxide or potassium hydroxide or aprotically, e.g. in the presence of iodotrimethylsilane, at temperatures between 0 and 120° C., preferably at temperatures between 10 and 100° C. A trifluoroacetyl group is preferably cleaved by treating with an acid such as hydrochloric acid, optionally in the presence of a solvent such as acetic acid at temperatures between 50 and 120° C. or by treating with sodium hydroxide solution optionally in the presence of a solvent such as tetrahydrofuran or methanol at temperatures between 0 and 50° C.

Any acetal or ketal protecting group used is cleaved for example hydrolytically in an aqueous solvent, e.g. in water, isopropanol/water, acetic acid/water, tetrahydrofuran/water or dioxane/water, in the presence of an acid such as trifluoroacetic acid, hydrochloric acid or sulphuric acid or aprotically, e.g. in the presence of iodotrimethylsilane, at temperatures between 0 and 120° C., preferably at temperatures between 10 and 100° C.

A trimethylsilyl group is cleaved for example in water, an aqueous solvent mixture or a lower alcohol such as methanol or ethanol in the presence of a base such as lithium hydroxide, sodium hydroxide, potassium carbonate or sodium methoxide.

In aqueous or alcoholic solvents, acids such as e.g. hydrochloric acid, trifluoroacetic acid or acetic acid are also suitable. For cleaving in organic solvents, such as for example diethyl ether, tetrahydrofuran or dichloromethane, it is also suitable to use fluoride reagents, such as e.g. tetrabutylammonium fluoride.

A benzyl, methoxybenzyl or benzyloxycarbonyl group is advantageously cleaved hydrogenolytically, e.g. with hydrogen in the presence of a catalyst such as palladium/charcoal in a suitable solvent such as methanol, ethanol, ethyl acetate or glacial acetic acid, optionally with the addition of an acid such as hydrochloric acid at temperatures between 0 and 100° C., but preferably at ambient temperatures between 20 and 60° C., and at a hydrogen pressure of 1 to 7 bar, but preferably 3 to 5 bar. A 2,4-dimethoxybenzyl group, however, is preferably cleaved in trifluoroacetic acid in the presence of anisole.

A tert.butyl or tert.butyloxycarbonyl group is preferably cleaved by treating with an acid such as trifluoroacetic acid or hydrochloric acid or by treating with iodotrimethylsilane optionally using a solvent such as methylene chloride, dioxane, methanol or diethylether.

In the reactions described hereinbefore, any reactive groups present such as ethynyl, hydroxy, amino, alkylamino or imino groups may be protected during the reaction by conventional protecting groups which are cleaved again after the reaction.

For example, a protecting group for an ethynyl group may be the trimethylsilyl or triisopropyl group. The 2-hydroxisoprop-2-yl group may also be used as a protective group.

For example, a protecting group for a hydroxy group may be a trimethylsilyl, acetyl, trityl, benzyl or tetrahydropyranyl group.

Protecting groups for an amino, alkylamino or imino group may be, for example, a formyl, acetyl, trifluoroacetyl, ethoxycarbonyl, tert.butoxycarbonyl, benzyloxycarbonyl, benzyl, methoxybenzyl or 2,4-dimethoxybenzyl group.

Moreover, the compounds of general formula I obtained may be resolved into their enantiomers and/or diastereomers, as mentioned hereinbefore. Thus, for example, cis/trans mixtures may be resolved into their cis and trans isomers, and compounds with at least one optically active carbon atom may be separated into their enantiomers.

Thus, for example, the cis/trans mixtures may be resolved by chromatography into the cis and trans isomers thereof, the compounds of general formula I obtained which occur as racemates may be separated by methods known per se (cf. Allinger N. L. and Eliel E. L. in "Topics in Stereochemistry", Vol. 6, Wiley Interscience, 1971) into their optical antipodes and compounds of general formula I with at least 2 asymmetric carbon atoms may be resolved into their diastereomers on the basis of their physical-chemical differences using methods known per se, e.g. by chromatography and/or fractional crystallisation, and, if these compounds are obtained in racemic form, they may subsequently be resolved into the enantiomers as mentioned above.

The enantiomers are preferably separated by column chromatography on chiral phases or by recrystallisation from an optically active solvent or by reacting with an optically active substance which forms salts or derivatives such as e.g. esters or amides with the racemic compound, particularly acids and the activated derivatives or alcohols thereof, and separating the diastereomeric mixture of salts or derivatives thus obtained, e.g. on the basis of their differences in solubility, whilst the free antipodes may be released from the pure diastereomeric salts or derivatives by the action of suitable agents. Optically active acids in common use are e.g. the D- and L-forms of tartaric acid or dibenzoyltartaric acid, di-o-tolyltartaric acid, malic acid, mandelic acid, camphorsulphonic acid, glutamic acid, aspartic acid or quinic acid. An optically active alcohol may be for example (+) or (−)-menthol and an optically active acyl group in amides, for example, may be a (+)-or (−)-menthyloxycarbonyl.

Furthermore, the compounds of formula I may be converted into the salts thereof, particularly for pharmaceutical use into the physiologically acceptable salts with inorganic or organic acids. Acids which may be used for this purpose include for example hydrochloric acid, hydrobromic acid, sulphuric acid, methanesulphonic acid, phosphoric acid, fumaric acid, succinic acid, lactic acid, citric acid, tartaric acid or maleic acid.

Moreover, the compounds obtained may be converted into mixtures, for example 1:1 or 1:2 mixtures with amino acids, particularly with alpha-amino acids such as proline or phenylalanine, which may have particularly favourable properties such as a high crystallinity.

The compounds according to the invention are advantageously also obtainable using the methods described in the examples that follow, which may also be combined for this purpose with methods known to the skilled man from the literature, for example, particularly the methods described in WO 98/31697, WO 01/27128, WO 02/083066, WO 03/099836 and WO 2004/063209.

As already mentioned, the compounds of general formula I according to the invention and the physiologically acceptable salts thereof have valuable pharmacological properties, particularly an inhibitory effect on the sodium-dependent glucose cotransporter SGLT, preferably SGLT2.

The biological properties of the new compounds may be investigated as follows:

The ability of the substances to inhibit the SGLT-2 activity may be demonstrated in a test set-up in which a CHO-K1 cell line (ATCC No. CCL 61) or alternatively an HEK293 cell line (ATCC No. CRL-1573), which is stably transfected with an expression vector pZeoSV (Invitrogen, EMBL accession number L36849), which contains the cDNA for the coding sequence of the human sodium glucose cotransporter 2 (Genbank Acc. No. NM_003041) (CHO-hSGLT2 or HEK-hSGLT2). These cell lines transport $^{14}C$-labelled alpha-methyl-glucopyranoside ($^{14}C$-AMG, Amersham) into the interior of the cell in sodium-dependent manner.

The SGLT-2 assay is carried out as follows:

CHO-hSGLT2 cells are cultivated in Ham's F12 Medium (BioWhittaker) with 10% foetal calf serum and 250 µg/mL zeocin (Invitrogen), and HEK293-hSGLT2 cells are cultivated in DMEM medium with 10% foetal calf serum and 250 μg/mL zeocin (Invitrogen). The cells are detached from the culture flasks by washing twice with PBS and subsequently treating with trypsin/EDTA. After the addition of cell culture medium the cells are centrifuged, resuspended in culture medium and counted in a Casy cell counter. Then 40,000 cells per well are seeded into a white, 96-well plate coated with poly-D-lysine and incubated overnight at 37° C., 5% $CO_2$. The cells are washed twice with 250 μl of assay buffer (Hanks Balanced Salt Solution, 137 mM NaCl, 5.4 mM KCl, 2.8 mM $CaCl_2$, 1.2 mM $MgSO_4$ and 10 mM HEPES (pH 7.4), 50 μg/mL of gentamycin). 250 μl of assay buffer and 5 μl of test compound are then added to each well and the plate is incubated for a further 15 minutes in the incubator. 5 μl of 10% DMSO are used as the negative control. The reaction is started by adding 5 μl of $^{14}C$-AMG (0.05 μCi) to each well. After 2 hours' incubation at 37° C., 5% $CO_2$, the cells are washed again with 250 μl of PBS (20° C.) and then lysed by the addition of 25 μl of 0.1 N NaOH (5 min. at 37° C.). 200 μl of MicroScint20 (Packard) are added to each well and incubation is continued for a further 20 min at 37° C. After this incubation the radioactivity of the $^{14}C$-AMG absorbed is measured in a Topcount (Packard) using a $^{14}C$ scintillation program.

To determine the selectivity with respect to human SGLT1 an analogous test is set up in which the cDNA for hSGLT1 (Genbank Acc. No. NM000343) instead of hSGLT2 cDNA is expressed in CHO-K1 or HEK293 cells.

The compounds of general formula I according to the invention may for example have EC50 values below 1000 nM, particularly below 200 nM, most preferably below 50 nM.

In view of their ability to inhibit the SGLT activity, the compounds of general formula I according to the invention and the corresponding pharmaceutically acceptable salts thereof are theoretically suitable for the treatment and/or preventative treatment of all those conditions or diseases which may be affected by the inhibition of the SGLT activity, particularly the SGLT-2 activity. Therefore, compounds according to the invention are particularly suitable for the prevention or treatment of diseases, particularly metabolic disorders, or conditions such as type 1 and type 2 diabetes mellitus, complications of diabetes (such as e.g. retinopathy, nephropathy or neuropathies, diabetic foot, ulcers, macroangiopathies), metabolic acidosis or ketosis, reactive hypoglycaemia, hyperinsulinaemia, glucose metabolic disorder, insulin resistance, metabolic syndrome, dyslipidaemias of different origins, atherosclerosis and related diseases, obesity, high blood pressure, chronic heart failure, edema and hyperuricaemia. These substances are also suitable for preventing beta-cell degeneration such as e.g. apoptosis or necrosis of pancreatic beta cells. The substances are also suitable for improving or restoring the functionality of pancreatic cells, and also of increasing the number and size of pancreatic beta cells. The compounds according to the invention may also be used as diuretics or antihypertensives and are suitable for the prevention and treatment of acute renal failure.

In particular, the compounds according to the invention, including the physiologically acceptable salts thereof, are suitable for the prevention or treatment of diabetes, particularly type 1 and type 2 diabetes mellitus, and/or diabetic complications.

In addition compounds according to the invention are particularly suitable for the prevention or treatment of overweight, obesity (including class I, class II and/or class III obesity), visceral obesity and/or abdominal obesity.

The dosage required to achieve the corresponding activity for treatment or prevention usually depends on the compound which is to be administered, the patient, the nature and gravity of the illness or condition and the method and frequency of administration and is for the patient's doctor to decide. Expediently, the dosage may be from 1 to 100 mg, preferably 1 to 30 mg, by intravenous route, and 1 to 1000 mg, preferably 1 to 100 mg, by oral route, in each case administered 1 to 4 times a day. For this purpose, the compounds of formula I prepared according to the invention may be formulated, optionally together with other active substances, together with one or more inert conventional carriers and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethylene glycol, propylene glycol, cetylstearyl alcohol, carboxymethylcellulose or fatty substances such as hard fat or suitable mixtures thereof, to produce conventional galenic preparations such as plain or coated tablets, capsules, powders, suspensions or suppositories.

The compounds according to the invention may also be used in conjunction with other active substances, particularly for the treatment and/or prevention of the diseases and conditions mentioned above. Other active substances which are suitable for such combinations include for example those which potentiate the therapeutic effect of an SGLT antagonist according to the invention with respect to one of the indications mentioned and/or which allow the dosage of an SGLT antagonist according to the invention to be reduced. Therapeutic agents which are suitable for such a combination include, for example, antidiabetic agents such as mefformin, sulphonylureas (e.g. glibenclamide, tolbutamide, glimepiride), nateglinide, repaglinide, thiazolidinediones (e.g. rosiglitazone, pioglitazone), PPAR-gamma-agonists (e.g. GI 262570) and antagonists, PPAR-gamma/alpha modulators (e.g. KRP 297), alpha-glucosidase inhibitors (e.g. acarbose, voglibose), DPPIV inhibitors (e.g. LAF237, MK-431), alpha2-antagonists, insulin and insulin analogues, GLP-1 and GLP-1 analogues (e.g. exendin-4) or amylin. The list also includes inhibitors of protein tyrosinephosphatase 1, substances that affect deregulated glucose production in the liver, such as e.g. inhibitors of glucose-6-phosphatase, or fructose-1,6-bisphosphatase, glycogen phosphorylase, glucagon receptor antagonists and inhibitors of phosphoenol pyruvate carboxykinase, glycogen synthase kinase or pyruvate dehydrokinase, lipid lowering agents such as for example HMG-CoA-reductase inhibitors (e.g. simvastatin, atorvastatin), fibrates (e.g. bezafibrate, fenofibrate), nicotinic acid and the derivatives thereof, PPAR-alpha agonists, PPAR-delta agonists, ACAT inhibitors (e.g. avasimibe) or cholesterol absorption inhibitors such as, for example, ezetimibe, bile acid-binding substances such as, for example, cholestyramine, inhibitors of ileac bile acid transport, HDL-raising compounds such as CETP inhibitors or ABC1 regulators or active substances for treating obesity, such as sibutramine or tetrahydrolipostatin, dexfenfluramine, axokine, antagonists of the cannabinoid1 receptor, MCH-1 receptor antagonists, MC4 receptor agonists, NPY5 or NPY2 antagonists or β3-agonists such as SB-418790 or AD-9677 and agonists of the 5HT2c receptor.

Moreover, combinations with drugs for influencing high blood pressure, chronic heart failure or atherosclerosis such as e.g. A-II antagonists or ACE inhibitors, ECE inhibitors, diuretics, β-blockers, Ca-antagonists, centrally acting antihypertensives, antagonists of the alpha-2-adrenergic receptor, inhibitors of neutral endopeptidase, thrombocyte aggregation inhibitors and others or combinations thereof are suitable. Examples of angiotensin II receptor antagonists are candesartan cilexetil, potassium losartan, eprosartan mesylate, valsartan, telmisartan, irbesartan, EXP-3174, L-158809, EXP-3312, olmesartan, medoxomil, tasosartan, KT-3-671, GA-0113, RU-64276, EMD-90423, BR-9701, etc. Angiotensin II receptor antagonists are preferably used for the treatment or prevention of high blood pressure and complications of diabetes, often combined with a diuretic such as hydrochlorothiazide.

A combination with uric acid synthesis inhibitors or uricosurics is suitable for the treatment or prevention of gout.

A combination with GABA-receptor antagonists, Na-channel blockers, topiramat, protein-kinase C inhibitors, advanced glycation end product inhibitors or aldose reductase inhibitors may be used for the treatment or prevention of complications of diabetes.

The dosage for the combination partners mentioned above is usefully 1/5 of the lowest dose normally recommended up to 1/1 of the normally recommended dose.

Therefore, in another aspect, this invention relates to the use of a compound according to the invention or a physiologically acceptable salt of such a compound combined with at least one of the active substances described above as a combination partner, for preparing a pharmaceutical composition which is suitable for the treatment or prevention of diseases or conditions which can be affected by inhibiting the sodium-dependent glucose cotransporter SGLT. These are preferably metabolic diseases, particularly one of the diseases or conditions listed above, most particularly diabetes or diabetic complications.

The use of the compound according to the invention, or a physiologically acceptable salt thereof, in combination with another active substance may take place simultaneously or at staggered times, but particularly within a short space of time. If they are administered simultaneously, the two active substances are given to the patient together; while if they are used at staggered times the two active substances are given to the patient within a period of less than or equal to 12 hours, but particularly less than or equal to 6 hours.

Consequently, in another aspect, this invention relates to a pharmaceutical composition which comprises a compound according to the invention or a physiologically acceptable salt of such a compound and at least one of the active substances described above as combination partners, optionally together with one or more inert carriers and/or diluents.

Thus, for example, a pharmaceutical composition according to the invention comprises a combination of a compound of formula I according to the invention or a physiologically acceptable salt of such a compound and at least one angiotensin II receptor antagonist optionally together with one or more inert carriers and/or diluents.

The compound according to the invention, or a physiologically acceptable salt thereof, and the additional active substance to be combined therewith may both be present together in one formulation, for example a tablet or capsule, or separately in two identical or different formulations, for example as a so-called kit-of-parts.

In the foregoing and following text, H atoms of hydroxyl groups are not explicitly shown in every case in structural formulae. The Examples that follow are intended to illustrate the present invention without restricting it:

Preparation of the Starting Compounds:

EXAMPLE I

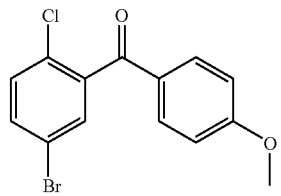

(5-Bromo-2-chloro-phenyl)-(4-methoxy-phenyl)-methanone 38.3 mL oxalyl chloride and 0.8 mL dimethylformamide are added to a mixture of 100 g 5-bromo-2-chloro-benzoic acid in 500 mL dichloromethane. The reaction mixture is stirred for 14 h, then filtered and separated from all volatile constituents in a rotary evaporator. The residue is dissolved in 150 mL dichloromethane, the solution is cooled to −5° C. and 46.5 g anisole are added. Then 51.5 g aluminum trichloride are added batchwise so that the temperature does not exceed 5° C. The solution is stirred for 1 h at 1-5° C. and then poured onto crushed ice. The organic phase is separated off and the aqueous phase is extracted with dichloromethane. The combined organic phases are washed with aqueous 1 M hydrochloric acid, twice with 1 M sodium hydroxide solution and with brine. Then the organic phase is dried over sodium sulfate, the solvent is removed and the residue is recrystallized from ethanol.

Yield: 86.3 g (64% of theory) Mass spectrum (ESI$^+$): m/z=325/327/329 (Br+Cl) [M+H]$^+$ The following compound may be obtained analogously to Example I:

(1) (5-bromo-2-methyl-phenyl)-(4-methoxy-phenyl)-methanone

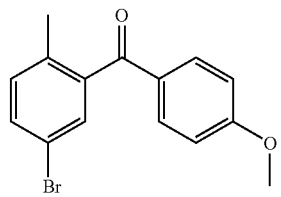

Mass spectrum (ESI$^+$): m/z=305/307 (Br) [M+H]$^+$

EXAMPLE II

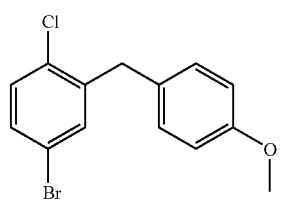

4-Bromo-1-chloro-2-(4-methoxy-benzyl)-benzene

A solution of 86.2 g (5-bromo-2-chloro-phenyl)-(4-methoxy-phenyl)-methanone and 101.5 mL triethylsilane in 75 mL dichloromethane and 150 mL acetonitrile is cooled to 10° C. Then with stirring 50.8 mL of boron trifluoride etherate are added so that the temperature does not exceed 20° C. The solution is stirred for 14 h at ambient temperature, before another 9 mL triethylsilane and 4.4 mL boron trifluoride etherate are added. The solution is stirred for a further 3 h period at 45-50° C. and then cooled to ambient temperature. A solution of 28 g potassium hydroxide in 70 mL water is added and the resultant mixture is stirred for 2 h. The organic phase is separated off and the aqueous phase is extracted another three times with diisopropylether. The combined organic phases are washed twice with 2 M potassium hydroxide solution and once with brine and then dried over sodium sulfate. After the solvent is evaporated, the residue is stirred in ethanol, separated again and dried at 60° C.

Yield: 50.0 g (61% of theory)

Mass spectrum (ESI$^+$): m/z=310/312/314 (Br+Cl) [M+H]$^+$

The following compound may be obtained analogously to Example II:

(1) 4-bromo-1-methyl-2-(4-methoxy-benzyl)-benzene

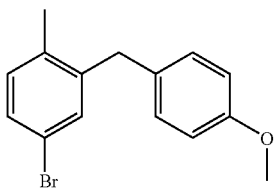

Mass spectrum (EI): m/z=290/292 (Br) [M]$^+$

EXAMPLE III

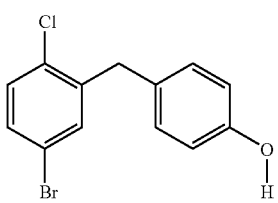

4-(5-bromo-2-chloro-benzyl)-phenol

A solution of 14.8 g 4-bromo-1-chloro-2-(4-methoxy-benzyl)-benzene in 150 mL dichloromethane is cooled in an ice bath. 50 mL of a 1 M solution of boron tribromide in dichloromethane are added and the resulting solution is stirred for 2 h at ambient temperature. The solution is then cooled in an ice bath again and saturated aqueous potassium carbonate solution is added dropwise. At ambient temperature the mixture is adjusted with aqueous 1 M hydrochloric acid to pH 1, the organic phase is separated off and the aqueous phase is extracted three times with ethyl acetate. The combined organic phases are dried over sodium sulfate and the solvent is removed completely.

Yield: 13.9 g (98% of theory)

Mass spectrum (ESI$^-$): m/z=295/297/299 (Br+Cl) [M−H]$^-$

The following compound may be obtained analogously to Example III:

(1) 4-(5-bromo-2-methyl-benzyl)-phenol

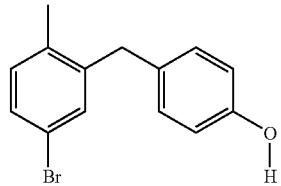

Mass spectrum (ESI$^-$): m/z=275/277 (Br) [M−H]$^-$

EXAMPLE IV

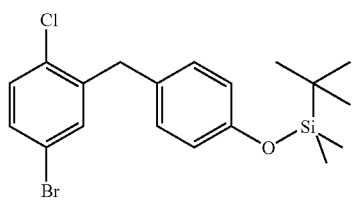

[4-(5-bromo-2-chloro-benzyl)-phenoxy]-tert-butyl-dimethyl-silane

A solution of 13.9 g 4-(5-bromo-2-chloro-benzyl)-phenol in 140 mL dichloromethane is cooled in an ice bath. Then 7.54 g tert-butyidimethylsilyl chloride in 20 mL dichloromethane are added followed by 9.8 mL triethylamine and 0.5 g dimethylaminopyridine. The resultant solution is stirred for 16 h at ambient temperature and then diluted with 100 mL dichloromethane. The organic phase is washed twice with aqueous 1 M hydrochloric acid and once with aqueous sodium hydrogen carbonate solution and then dried over sodium sulfate. After the solvent is removed, the residue is filtered through silica gel (cyclohexane/ethyl acetate 100:1).

Yield: 16.8 g (87% of theory)

Mass spectrum (EI): m/z=410/412/414 (Br+Cl) [M]$^+$

The following compound may be obtained analogously to Example IV:

(1) [4-(5-bromo-2-methyl-benzyl)-phenoxy]-tert-butyl-dimethyl-silane

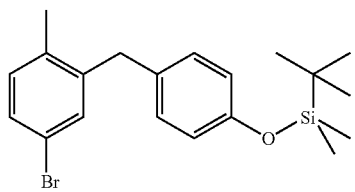

Mass spectrum (ESI$^+$): m/z=391/393 (Br) [M+H]$^+$

EXAMPLE V

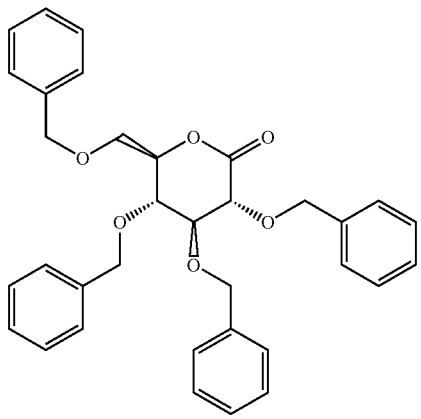

2,3,4,6-Tetra-O-benzyl-D-glucopyranone

To a solution of 10.0 g 2,3,4,6-tetra-O-benzyl-α-D-glucopyranose in 140 mL dichloromethane are added 4 g freshly activated molecular sieves 4 Å and 3.3 g N-methylmorpholine-N-oxide.

The solution is stirred for 20 min at ambient temperature, before 0.3 g tetra-n-propylammonium perruthenate are added. After 2 h stirring at ambient temperature the solution is diluted with dichloromethane and filtered through Celite. The filtrate is washed with aqueous sodium thiosulfate solution and water and then dried over sodium sulfate. After the solvent is evaporated, the residue is chromatographed on silica gel (cyclohexane/ethyl acetate 4:1).

Yield: 8.2 g (82% of theory)
Mass spectrum (ESI$^+$): m/z=539 [M+H]$^+$

EXAMPLE VI

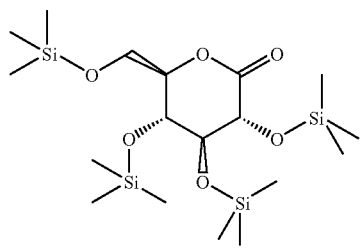

2,3,4,6-tetrakis-O-(trimethylsilyl)-D-glucopyranone

A solution of 20 g D-glucono-1,5-lactone and 98.5 mL N-methylmorpholine in 200 mL of tetrahydrofuran is cooled to −5° C. Then 85 mL trimethylsilyl chloride are added dropwise so that the temperature does not exceed 5° C. The solution is then stirred for 1 h at ambient temperature, 5 h at 35° C. and again for 14 h at ambient temperature. After the addition of 300 mL of toluene the solution is cooled in an ice bath and 500 mL of water are added so that the temperature does not exceed 10° C. The organic phase is then separated and washed with aqueous sodium dihydrogen phosphate solution, water and brine. The solvent is removed and the residue azeotropically dried using toluene.

Yield: 52.5 g (approx. 90% pure)
Mass spectrum (ESI$^+$): m/z=467 [M+H]$^+$

EXAMPLE VII

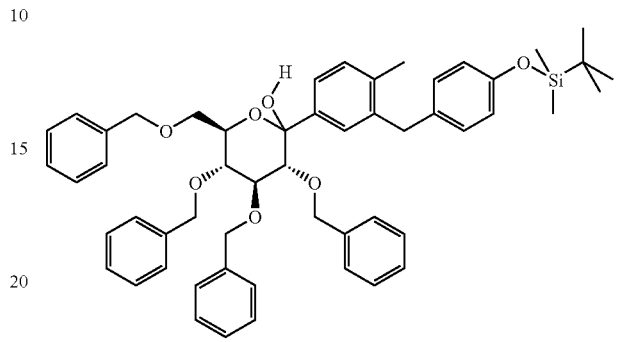

1-(2,3,4,6-Tetra-O-benzyl-1-hydroxy-D-glucopyranos-1-yl)-3-[4-(tert-butyl-dimethyl-silyloxy)-benzyl]-4-methyl-benzene A solution of 0.34 g [4-(5-bromo-2-methyl-benzyl)-phenoxy]-tert-butyl-dimethyl-silane in 3 mL dry tetrahydrofuran is cooled to −80° C. under argon. 0.54 mL of a 1.6 M solution of n-butyllithium in hexane are added dropwise and the resulting solution is stirred for 1.5 h at −78° C. A solution of 0.43 g 2,3,4,6-tetra-O-benzyl-D-glucopyranone in 2.5 mL of tetrahydrofuran chilled to −80° C. is added dropwise to this solution by means of a transfer needle. The resulting solution is stirred for 5 h at −78° C. The reaction is quenched with a solution of 0.1 mL acetic acid in 1 mL of tetrahydrofuran and warmed to ambient temperature. Then aqueous sodium hydrogen carbonate solution is added and the mixture is extracted four times with ethyl acetate. The organic phases are dried over sodium sulfate and the solvent is evaporated. The residue is purified by chromatography on silica gel (cyclohexane/ethyl acetate 15:1->4:1).

Yield: 0.48 g (approx. 88% pure)
Mass spectrum (ESI$^+$): m/z=868 [M+H]$^+$

EXAMPLE VIII

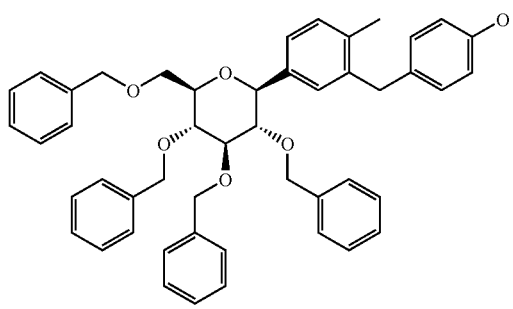

1-(2,3,4,6-tetra-O-benzyl-β-D-glucopyranos-1-yl)-3-(4-hydroxy-benzyl)-4-methyl-benzene A solution of 0.48 g (approx. 88% pure) 1-(2,3,4,6-tetra-O-benzyl-1-hydroxy-D-glucopyranosyl)-3-[4-(tert-butyl-dimethyl-silyloxy)-benzyl]-4-methyl-benzene in 3.5 mL dry acetonitrile is cooled to −40° C. under argon. 0.13 mL triisopropylsilane and 0.08 mL boron trifluoride etherate are added dropwise. The solution is stirred for 3 h at −35° C., before another 0.02 mL of triisopropylsilane and 0.01 mL of boron trifluoride etherate are added. After a further 2 h at −40° C. aqueous potassium carbonate solution is added, and the resulting mixture is stirred for 1 h at ambient temperature. Then water is added and the mixture is extracted four times with ethyl acetate. The organic phase is dried over sodium sulfate, concentrated and chromatographed on silica gel (cyclohexane/ethyl acetate 10:1->4:1).

Yield: 0.24 g (68% of theory).
Mass spectrum (ESI+): m/z=738 [M+NH$_4$]+

EXAMPLE IX

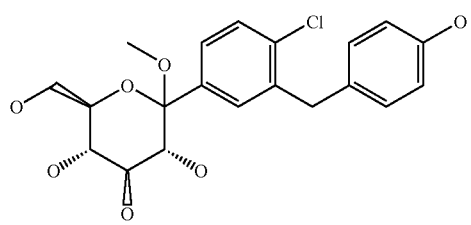

1-Chloro-4-(1-methoxy-D-glucopyranos-1-yl)-2-(4-hydroxy-benzyl)-benzene

A solution of 14.0 g [4-(5-bromo-2-chloro-benzyl)-phenoxy]-tert-butyl-dimethyl-silane in 150 mL hexane and 30 mL tetrahydrofuran is cooled to −80° C. under argon atmosphere. 11.8 mL of a −70° C.-cold solution of tert-butyl-lithium in pentane (1.7 M) are added dropwise to the bromobenzene solution and the resulting solution is stirred for 45 min at −80° C. Then a −70° C.-cold solution of 18.1 g of 2,3,4,6-tetrakis-O-(trimethylsilyl)-D-glucopyranone in 50 mL hexane is added. The resulting solution is stirred for 1 h at −70° C. 150 mL 1% aqueous acetic acid solution is added and the cooling bath is removed. After the reaction solution is warmed to room temperature, the organic phase is separated and the aqueous phase is extracted with ethyl acetate. After drying the combined organic phases over sodium sulfate, the solvent is evaporated and the residue is dissolved in 150 mL methanol. The resultant solution is treated with 1 mL methanesulfonic acid and stirred at room temperature for 16 h. The reaction solution is neutralized with aqueous sodium bicarbonate solution, most of the methanol is evaporated and the aqueous residue is extracted with ethyl acetate. The combined organic phases are dried over sodium sulfate and the solvent is evaporated. The residue is dissolved in as little methanol and ethyl acetate as possible and the resulting solution is added to petrol ether. The precipitate is separated by filtration and dried at 50° C.

Yield: 10.0 g (72% of theory)
Mass spectrum (ESI+): m/z=433/435 (Cl) [M+Na]+

The following compound may be obtained analogously to Example IX:

(1) 1-methyl-4-(1-methoxy-D-glucopyranos-1-yl)-2-(4-hydroxy-benzyl)-benzene

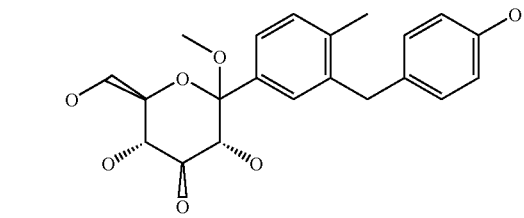

Mass spectrum (ESI−): m/z=389 [M−H]−

EXAMPLE X

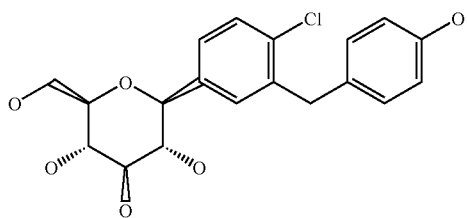

1-Chloro-4-(β-D-glucopyranos-1-yl)-2-(4-hydroxy-benzyl)-benzene

A solution of 25.0 g 1-chloro-4-(1-methoxy-D-glucopyranos-1-yl)-2-(4-hydroxy-benzyl)-benzene and 20.0 mL triethylsilane in 120 mL dichloromethane and 360 mL acetonitrile is cooled to −5-−10° C. 10.0 mL Boron trifluoride etherate are added dropwise and the solution is stirred in the cooling bath for 1 h. Aqueous sodium hydrogen carbonate solution is added, the organic phase is separated and the aqueous phase is extracted with ethyl acetate. The combined organic phases are dried over sodium sulfate and the solvent is removed in vacuo. The residue is washed with diisopropylether and dissolved in as little ethyl acetate as needed. The resulting solution is treated with cyclohexane and the precipitate is separated by filtration and dried at 50° C.

Yield: 23.0 g (99% of theory, ca. 7:1 mixture with α-anomer)
Mass spectrum (ESI−): m/z=425/427 (Cl) [M+HCOO]−

The following compound may be obtained analogously to Example X:

(1) 1-methyl-4-(β-D-glucopyranos-1-yl)-2-(4-hydroxy-benzyl)-benzene

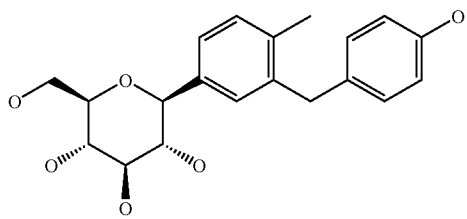

Mass spectrum (ESI+): m/z=378 [M+NH$_4$]+

EXAMPLE XI

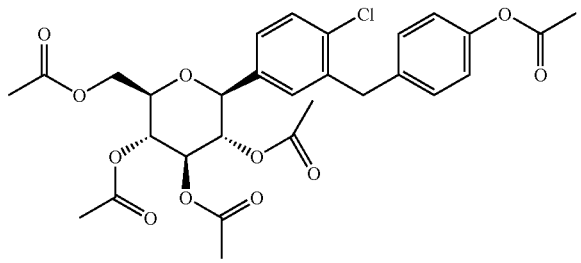

1-Chloro-4-(2,3,4,6-tetra-O-acetyl-β-D-glucopyranos-1-yl)-2-(4-acetoxy-benzyl)-benzene To a solution of 23.0 g 1-chloro-4-(β-D-glucopyranos-1-yl)-2-(4-hydroxy-benzyl)-benzene and 55 mL pyridine in 200 mL dichloromethane is added 60 mL acetic acid anhydride followed by 0.1 g 4-dimethylaminopyridine. The solution is stirred for 1 h at ambient temperature. Then, the solution is diluted with dichloromethane and washed with 2 M aqueous hydrochloric acid. The organic phase is dried over sodium sulfate and the solvent is evaporated. The residue is recrystallized from ethanol to give the pure β-anomer as a white solid.

Yield: 7.8 g (22% of theory)

Mass spectrum (ESI$^+$): m/z=608/610 (Cl) [M+NH$_4$]$^+$

The following compound may be obtained analogously to Example XI:

(1) 1-Methyl-4-(2,3,4,6-tetra-O-acetyl-β-D-glucopyranos-1-yl)-2-(4-acetoxy-benzyl)-benzene

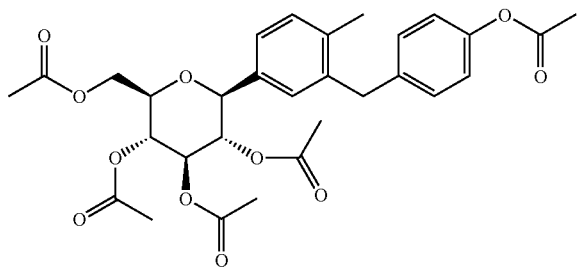

Mass spectrum (ESI$^+$): m/z=588 [M+NH$_4$]$^+$

EXAMPLE XII

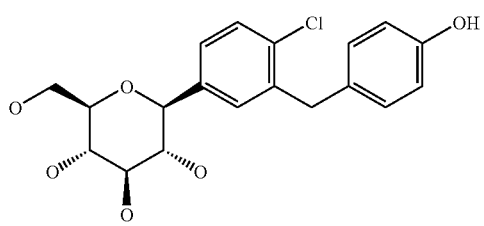

1-Chloro-4-(β-D-glucopyranos-1-yl)-2-(4-hydroxy-benzyl)-benzene

To a solution of 7.9 g 1-chloro-4-(2,3,4,6-tetra-O-acetyl-β-D-glucopyranos-1-yl)-2-(4-acetoxy-benzyl)-benzene in 150 mL methanol is added 25 mL 4 M aqueous potassium hydroxide solution. The solution is stirred at room temperature for 1 h and then adjusted to pH 5 with 4 M hydrochloric acid. Most of the methanol is evaporated and the remaining solution is extracted with ethyl acetate. The combined extracts are dried over sodium sulfate and the solvent is removed in vacuo.

Yield: 5.1 g (100% of theory)

Mass spectrum (ESI$^+$): m/z=398/400 (Cl) [M+NH$_4$]$^+$

The following compound may be obtained analogously to Example XII:

(1) 1-Methyl-4-(β-D-glucopyranos-1-yl)-2-(4-hydroxy-benzyl)-benzene

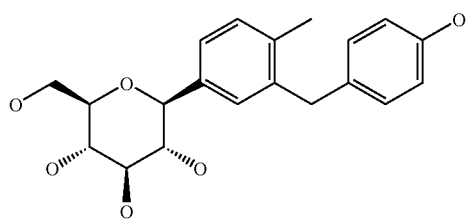

Mass spectrum (ESI$^+$): m/z=378 [M+NH$_4$]$^+$

Preparation of the End Compounds:

EXAMPLE 1

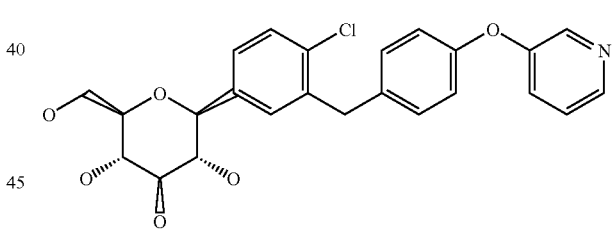

1-Chloro-4-(β-D-glucopyranos-1-yl)-2-[4-(pyridin-3-yloxy)-benzyl]-benzene

To an argon-purged flask charged with 0.43 g cesium carbonate and 1 mL N-methylpyrrolidinone are added 0.28 g 3-iodopyridine, 12 mg 2,2,6,6-tetramethylhepta-3,5-dione and 34 mg copper(I) chloride. The flask is tightly sealed and the mixture is stirred at 120° C over night. After cooling the reaction mixture to room temperature, the solvent is evaporated and the residue purified by chromatography on silica gel (dichloromethane/methanol 1:0->5:1).

Yield: 82 mg (14% of theory)

Mass spectrum (ESI$^+$): m/z=458/460 (Cl) [M+H]$^+$

The following compounds may be obtained analogously to Example 1:

(2) 1-Chloro-4-(β-D-glucopyranos-1-yl)-2-[4-(pyrimidin-5-yloxy)-benzyl]-benzene

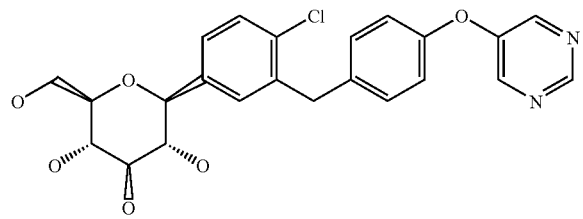

Mass spectrum (ESI⁺): m/z=459/461 (Cl) [M+H]⁺

The compound is obtained from 1-chloro-4-(β-D-glucopyranos-1-yl)-2-(4-hydroxy-benzyl)-benzene and 5-bromo-pyrimidine.

(3) 1-Chloro-4-(β-D-glucopyranos-1-yl)-2-[4-(pyridin-2-yloxy)-benzyl]-benzene

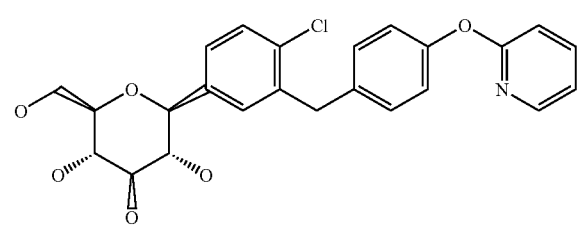

Mass spectrum (ESI⁺): m/z=458/460 (Cl) [M+H]⁺

The compound is obtained from 1-chloro-4-(β-D-glucopyranos-1-yl)-2-(4-hydroxy-benzyl)-benzene and 2-bromo-pyridine.

(4) 1-Chloro-4-(β-D-glucopyranos-1-yl)-2-[4-(pyridin-4-yloxy)-benzyl]-benzene

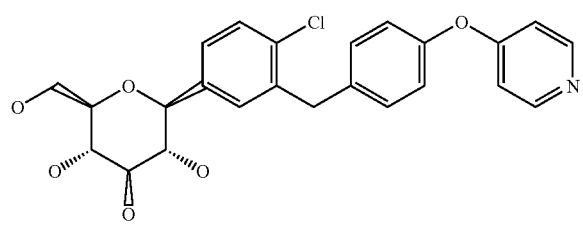

Mass spectrum (ESI⁺): m/z=458/460 (Cl) [M+H]⁺

The compound is obtained from 1-chloro-4-(β-D-glucopyranos-1-yl)-2-(4-hydroxy-benzyl)-benzene and 4-iodo-pyridine.

(5) 1-Chloro-4-(β-D-glucopyranos-1-yl)-2-[4-(pyrimidin-2-yloxy)-benzyl]-benzene

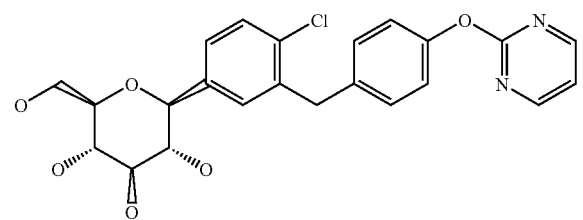

Mass spectrum (ESI⁺): m/z=459/461 (Cl) [M+H]⁺

The compound is obtained from 1-chloro-4-(β-D-glucopyranos-1-yl)-2-(4-hydroxy-benzyl)-benzene and 2-bromo-pyrimidine.

(6) 1-Chloro-4-(β-D-glucopyranos-1-yl)-2-[4-(6-methyl-pyridazin-3-yloxy)-benzyl]-benzene

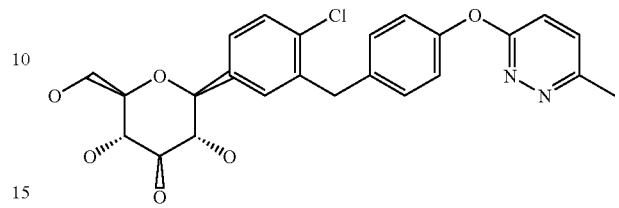

Mass spectrum (ESI⁺): m/z=473/475 (Cl) [M+H]⁺

The compound is obtained from 1-chloro-4-(β-D-glucopyranos-1-yl)-2-(4-hydroxy-benzyl)-benzene and 3-iodo-6-methyl-pyridazine.

(7) 1-Chloro-4-(β-D-glucopyranos-1-yl)-2-[4-(pyrazin-2-yloxy)-benzyl]-benzene

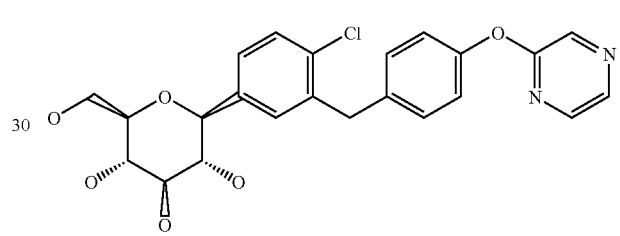

Mass spectrum (ESI⁺): m/z=459/461 (Cl) [M+H]⁺

The compound is obtained from 1-chloro-4-(β-D-glucopyranos-1-yl)-2-(4-hydroxy-benzyl)-benzene and 2-iodo-pyrazine.

(8) 1-Chloro-4-(β-D-glucopyranos-1-yl)-2-[4-(6-methoxy-pyridazin-3-yloxy)-benzyl]-benzene

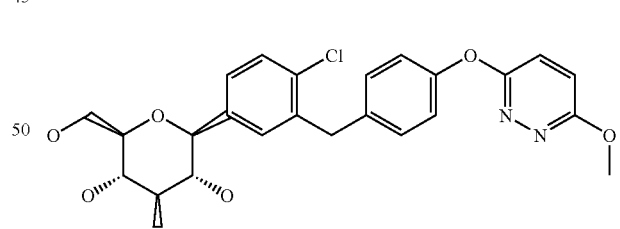

Mass spectrum (ESI⁺): m/z=489/491 (Cl) [M+H]⁺

The compound is obtained from 1-chloro-4-(β-D-glucopyranos-1-yl)-2-(4-hydroxy-benzyl)-benzene and 3-iodo-6-methoxy-pyridazine.

The following compounds are also prepared analogously to the above-mentioned Examples and other methods known from the literature:

| Ex. | Structure |
|---|---|
| 9 | 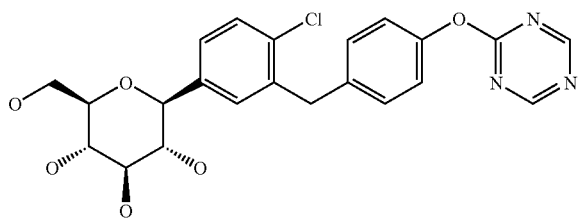 |
| 10 | 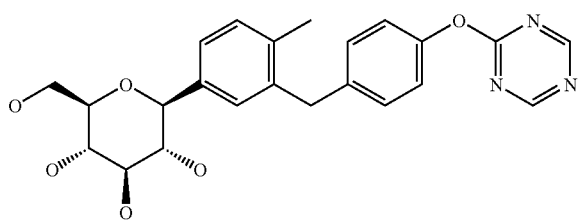 |
| 11 | 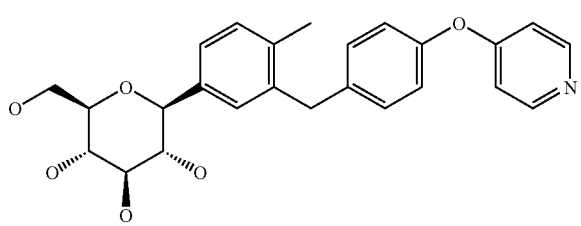 |
| 12 | 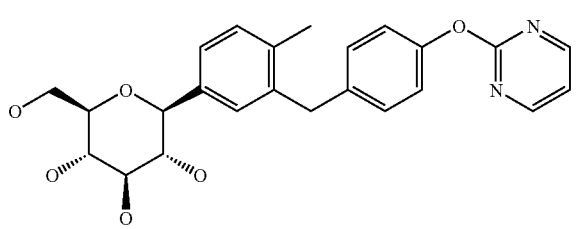 |
| 13 | 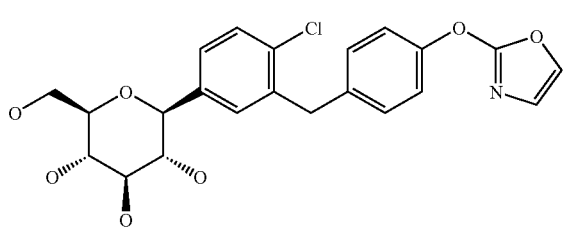 |
| 14 | 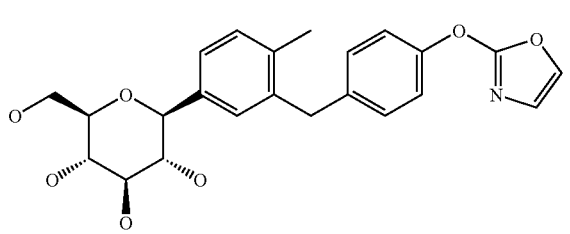 |
| 15 | 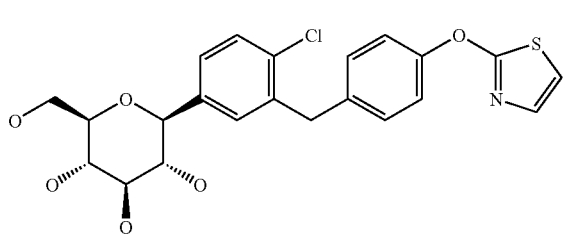 |

-continued
| Ex. | Structure |
|---|---|
| 16 | 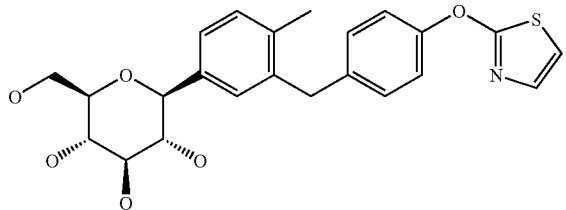 |
| 17 | 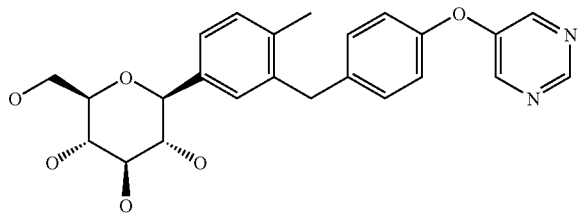 |
| 18 | 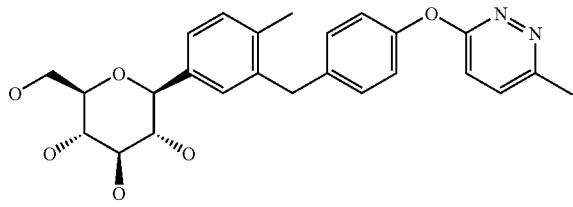 |
| 19 | 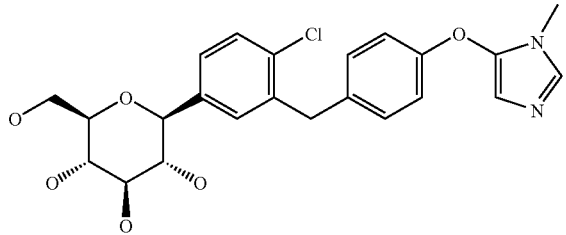 |
| 20 | 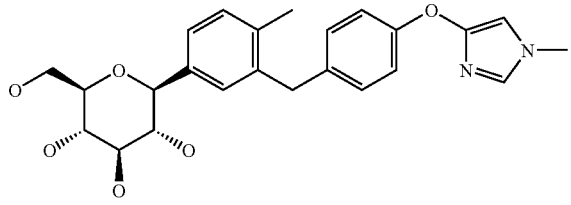 |
| 21 | 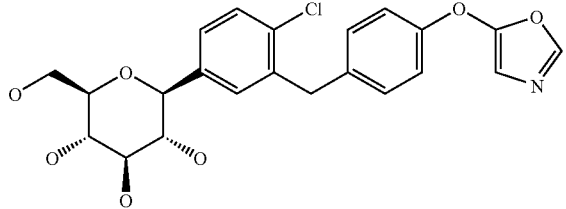 |

-continued
| Ex. | Structure |
|---|---|
| 22 | 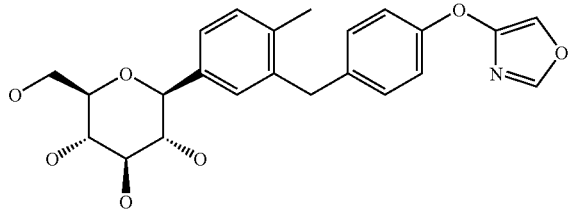 |
| 23 | 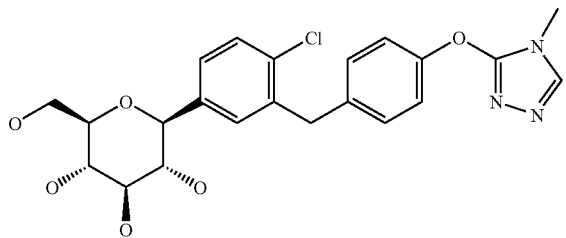 |
| 24 | 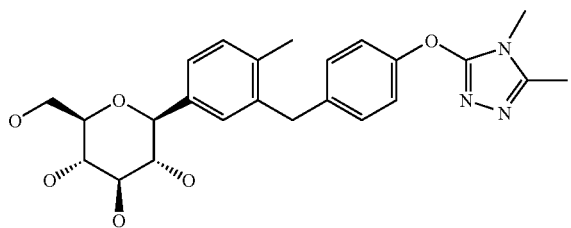 |
| 25 | 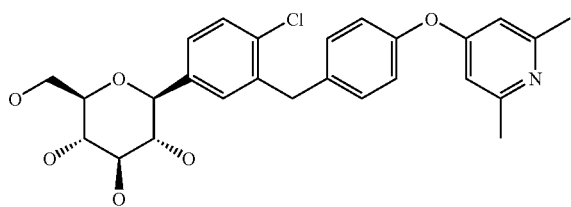 |
| 26 | 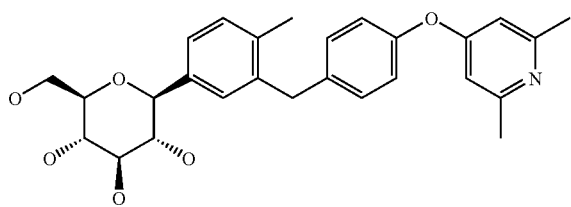 |
| 27 | 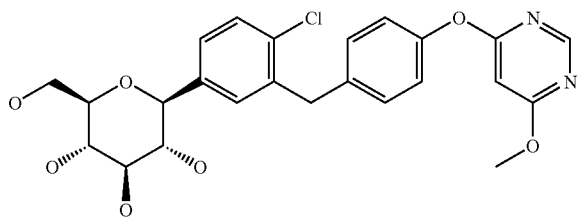 |
| 28 | 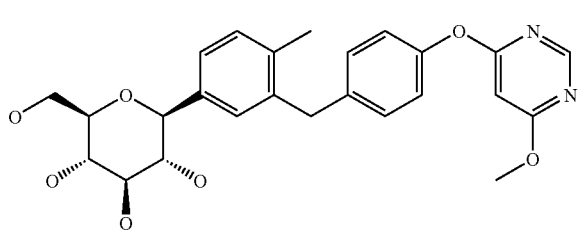 |

-continued
| Ex. | Structure |
|---|---|
| 29 | 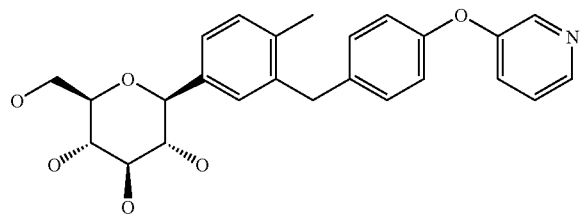 |
| 30 | 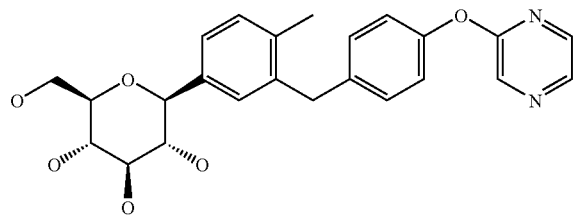 |
| 31 | 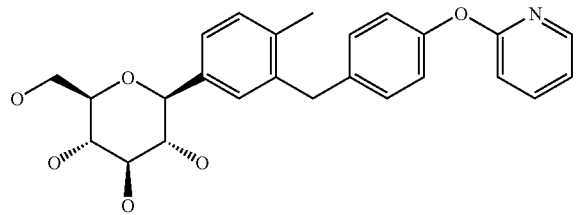 |
| 32 | 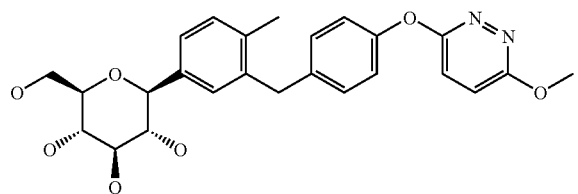 |
| 33 | 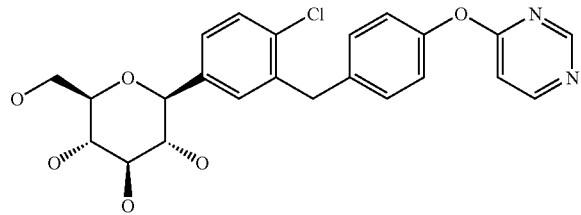 |
| 34 | 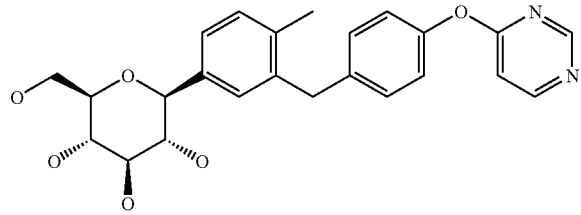 |

Some examples of formulations will now be described in which the term "active substance" denotes one or more compounds according to the invention, including the salts thereof. In the case of one of the combinations with one or additional active substances as described previously, the term "active substance" also includes the additional active substances.

EXAMPLE A

Tablets Containing 100 mg of Active Substance

| Composition: 1 tablet contains: | |
|---|---|
| active substance | 100.0 mg |
| lactose | 80.0 mg |
| corn starch | 34.0 mg |
| polyvinylpyrrolidone | 4.0 mg |
| magnesium stearate | 2.0 mg |
| | 220.0 mg |

Method of Preparation:

The active substance, lactose and starch are mixed together and uniformly moistened with an aqueous solution of the polyvinylpyrrolidone. After the moist composition has been screened (2.0 mm mesh size) and dried in a rack-type drier at 50° C. it is screened again (1.5 mm mesh size) and the lubricant is added. The finished mixture is compressed to form tablets.

Weight of tablet: 220 mg

Diameter: 10 mm, biplanar, facetted on both sides and notched on one side.

EXAMPLE B

Tablets Containing 150 mg of Active Substance

| Composition: 1 tablet contains: | |
|---|---|
| active substance | 150.0 mg |
| powdered lactose | 89.0 mg |
| corn starch | 40.0 mg |
| colloidal silica | 10.0 mg |
| polyvinylpyrrolidone | 10.0 mg |
| magnesium stearate | 1.0 mg |
| | 300.0 mg |

Preparation:

The active substance mixed with lactose, corn starch and silica is moistened with a 20% aqueous polyvinylpyrrolidone solution and passed through a screen with a mesh size of 1.5 mm. The granules, dried at 45° C., are passed through the same screen again and mixed with the specified amount of magnesium stearate. Tablets are pressed from the mixture.

Weight of tablet: 300 mg die: 10 mm, flat

EXAMPLE C

Hard Gelatine Capsules Containing 150 mg of Active Substance

| Composition: 1 capsule contains: | | |
|---|---|---|
| active substance | | 150.0 mg |
| corn starch (dried) | approx. | 180.0 mg |
| lactose (powdered) | approx. | 87.0 mg |
| magnesium stearate | | 3.0 mg |
| | approx. | 420.0 mg |

Preparation:

The active substance is mixed with the excipients, passed through a screen with a mesh size of 0.75 mm and homogeneously mixed using a suitable apparatus. The finished mixture is packed into size 1 hard gelatine capsules.

Capsule filling: approx. 320 mg

Capsule shell: size 1 hard gelatine capsule.

EXAMPLE D

Suppositories Containing 150 mg of Active Substance

| Composition: 1 suppository contains: | |
|---|---|
| active substance | 150.0 mg |
| polyethyleneglycol 1500 | 550.0 mg |
| polyethyleneglycol 6000 | 460.0 mg |
| polyoxyethylene sorbitan monostearate | 840.0 mg |
| | 2,000.0 mg |

Preparation:

After the suppository mass has been melted the active substance is homogeneously distributed therein and the melt is poured into chilled moulds.

EXAMPLE E

Ampoules Containing 10 mg Active Substance

| Composition: | |
|---|---|
| active substance | 10.0 mg |
| 0.01 N hydrochloric acid q.s. | |
| double-distilled water | ad 2.0 mL |

Preparation:

The active substance is dissolved in the necessary amount of 0.01 N HCl, made isotonic with common salt, filtered sterile and transferred into 2 mL ampoules.

EXAMPLE F

Ampoules Containing 50 mg of Active Substance

| Composition: | |
|---|---|
| active substance | 50.0 mg |
| 0.01 N hydrochloric acid q.s. | |
| double-distilled water | ad 10.0 mL |

Preparation:

The active substance is dissolved in the necessary amount of 0.01 N HCl, made isotonic with common salt, filtered sterile and transferred into 10 mL ampoules.

The invention claimed is:

1. A glucopyranosyl-substituted (heteroaryloxy-benzyl)-benzene compound of general formula I

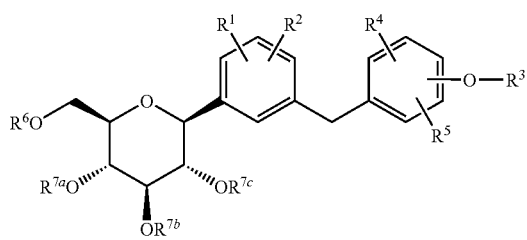

wherein $R^1$ denotes hydrogen, fluorine, chlorine, bromine, iodine, $C_{1-4}$-alkyl, $C_{2-6}$-alkynyl, $C_{1-4}$-alkoxy, $C_{2-4}$-alkenyl-$C_{1-4}$-alkoxy, $C_{2-4}$-alkynyl-$C_{1-4}$-alkoxy, methyl substituted by 1 to 3 fluorine atoms, ethyl substituted by 1 to 5 fluorine atoms, methoxy substituted by 1 to 3 fluorine atoms, ethoxy substituted by 1 to 5 fluorine atoms, $C_{1-4}$-alkyl substituted by a hydroxy or $C_{1-3}$-alkoxy group, $C_{2-4}$-alkoxy substituted by a hydroxy or $C_{1-3}$-alkoxy group, $C_{2-6}$-alkenyl, $C_{3-7}$-cycloalkyl, $C_{3-7}$-cycloalkyl-$C_{1-3}$-alkyl, $C_{3-7}$-cycloalkyloxy, $C_{3-7}$-cycloalkyl-$C_{1-3}$-alkoxy, $C_{5-7}$-cycloalkenyloxy, hydroxy, amino, nitro or cyano, while in the $C_{5-6}$-cycloalkyl groups a methylene group may be replaced by O;

$R^2$ denotes hydrogen, fluorine, chlorine, bromine, hydroxy, $C_{1-4}$-alkyl, $C_{1-4}$-alkoxy, cyano or nitro, while the alkyl or alkoxy group may be mono- or polysubstituted by fluorine, and $R^3$ denotes a 5- or 6-membered monocyclic heteroaryl-group which has 1 to 4 heteroatoms independently selected from the group consisting of N, O and S; or a 8-, 9- or 10-membered bicyclic heteroaryl-group which has 1 to 4 heteroatoms independently selected from the group consisting of N, O and S; and wherein the ring of the bicyclic heteroaryl-group attached to the ether oxygen of the group —O—$R^3$ is heteroaromatic; and wherein said heteroaryl-groups may possess 1 or 2 carbonyl groups as part of the mono- or bicyclic heteroaromatic ring-system; and wherein an N-atom of said heteroaryl-groups may be oxidized to form the corresponding N-oxide; and wherein one or more methine groups in said heteroaryl-groups may be substituted independently of one another with a substituent L1; and wherein one or more imino-groups in said heteroaryl-groups may be substituted independently of one another with a substituent $R^N$; and $R^4$, $R^5$ independently of one another denote hydrogen, fluorine, chlorine, bromine, iodine, cyano, nitro, $C_{1-3}$-alkyl, $C_{1-3}$-alkoxy or a methyl- or methoxy-group substituted by 1 to 3 fluorine atoms, L1 independently of one another are selected from among fluorine, chlorine, bromine, iodine, hydroxy, cyano, $C_{1-3}$-alkyl, difluoromethyl, trifluoromethyl, $C_{1-3}$-alkoxy, difluoromethoxy, trifluoromethoxy, amino, $C_{1-3}$-alkyl-amino and di($C_{1-3}$-alkyl)-amino; and $R^N$ independently of one another are selected from among $C_{1-3}$-alkyl; and $R^6$, $R^{7a}$, $R^{7b}$, $R^{7c}$ independently of one another have a meaning selected from among hydrogen, ($C_{1-18}$-alkyl)carbonyl, ($C_{1-18}$-alkyl)oxycarbonyl, arylcarbonyl and aryl-($C_{1-3}$-alkyl)-carbonyl, while the aryl-groups may be mono- or disubstituted independently of one another by identical or different groups L1;

while by the aryl groups mentioned in the definition of the above groups are meant phenyl or naphthyl groups which may be substituted as defined; and while, unless otherwise stated, the above-mentioned alkyl groups may be straight-chain or branched, the tautomers, the stereoisomers thereof, the mixtures thereof and the salts thereof.

2. A glucopyranosyl-substituted (heteroaryloxy-benzyl)-benzene compound of general formula I.2

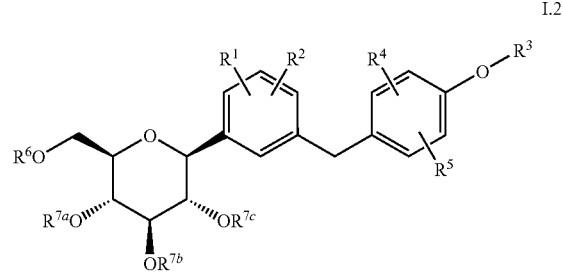

wherein the groups $R^1$ to $R^6$ and $R^{7a}$, $R^{7b}$ and $R^{7c}$ are defined as in claim 1.

3. A glucopyranosyl-substituted (heteroaryloxy-benzyl)-benzene compound according to claim 1, characterised in that the group $R^3$ is a 5- or 6-membered monocyclic heteroaryl-group wherein the term 5- or 6-membered monocyclic heteroaryl-group denotes a pyrrolyl, furanyl, thienyl, pyridyl or tetrazolyl group, or a pyrrolyl, furanyl, thienyl or pyridyl group wherein one or two methine groups are replaced in each case by a nitrogen atom, wherein the heteroaryl-group may possess 1 or 2 carbonyl groups as part of the heteroaromatic ring-system; and wherein an N-atom of the heteroaryl group may be oxidized to form the corresponding N-oxide; and wherein one or more methine-groups of the heteroaryl-group may be substituted independently of one another with a substituent L1; and wherein one or more imino-groups of the heteroaryl-group may be substituted independently of one another with a substituent $R^N$;

wherein L1 and $R^N$ are defined as in claim 1.

4. A glucopyranosyl-substituted (heteroaryloxy-benzyl)-benzene compound according to claim 1, characterised in that the group $R^1$ denotes hydrogen, fluorine, chlorine, bromine, $C_{1-4}$-alkyl, $C_{1-4}$-alkoxy, methyl substituted by 1 to 3 fluorine atoms, methoxy substituted by 1 to 3 fluorine atoms, $C_{3-7}$-cycloalkyloxy or $C_{3-7}$-cycloalkyl-$C_{1-3}$-alkoxy, while in the $C_{5-6}$-cycloalkyl groups a methylene group may be replaced by O.

5. A glucopyranosyl-substituted (heteroaryloxy-benzyl)-benzene compound according to claim 1, characterised in that the group $R^2$ denotes hydrogen, fluorine, chlorine, methyl, methoxy, ethoxy and methyl substituted by 1 to 3 fluorine atoms.

6. A glucopyranosyl-substituted (heteroaryloxy-benzyl)-benzene compound according to claim 1, characterised in that the groups $R^4$ and/or $R^5$ independently of one another represent hydrogen or fluorine.

7. A glucopyranosyl-substituted (heteroaryloxy-benzyl)-benzene compound according to claim 1, characterised in that the group $R^6$ denotes hydrogen, $(C_{1-8}$-alkyl)oxycarbonyl, $C_{1-8}$-alkylcarbonyl or benzoyl, preferably hydrogen.

8. A glucopyranosyl-substituted (heteroaryloxy-benzyl)-benzene compound according to claim 1, characterised in that the groups $R^{7a}$, $R^{7b}$, $R^{7c}$ represent hydrogen.

9. A physiologically acceptable salt of a compound according to claim 1 further comprised of inorganic or organic acids.

10. A pharmaceutical composition, containing a compound according to claim 1 optionally together with one or more inert carriers and/or diluents.

11. A method of treating metabolic disorders, said method comprised of the step of administering to a patient in need thereof a therapeutically effective amount of a compound according to claim 1 or a pharmaceutically acceptable salt thereof, wherein the metabolic disorder is selected from the group consisting of type 1 and type 2 diabetes mellitus, complications of diabetes, metabolic acidosis or ketosis, reactive hypoglycaemia, hyperinsulinaemia, glucose metabolic disorder, insulin resistance, metabolic syndrome, dyslipidaemias of different origins, atherosclerosis and related diseases, obesity, high blood pressure, chronic heart failure, edema and hyperuricaemia.

12. A method of inhibiting sodium-dependent cotrasporter SGLT2 said method comprised of the step of administering to a patient in need thereof a therapeutically effective amount of a composition according to claim 1 or a pharmaceutically acceptable salt thereof.

13. A method for improving and/or restoring the functionality of pancreatic beta cells said method comprised of the steps of administering to a patient in need thereof a therapeutically effective amount of a compound according to claim 1 or a pharmaceutically acceptable salt thereof.

14. A process for preparing a pharmaceutical composition according to claim 1, wherein said compound is incorporated in one or more inert carriers and/or diluents by a non-chemical method.

15. A process for preparing the compounds of general formula I according to claim 1 wherein $R^6$, $R^{7a}$, $R^{7b}$ and $R^{7c}$ represent hydrogen, characterised in that a compound of general formula III

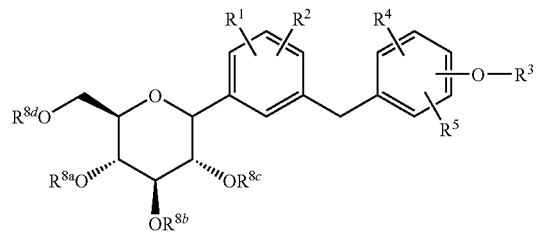

wherein $R^{8a}$, $R^{8b}$, $R^{8c}$, $R^{8d}$ independently of one another have one of the meanings given for the groups $R^5$, $R^{7a}$, $R^{7b}$, $R^{7c}$, but at least one of the groups $R^{8a}$, $R^{8b}$, $R^{8c}$, $R^{8d}$ does not denote hydrogen, or denotes a benzyl group or a $R^aR^bR^cSi$ group or a ketal or acetal group, while in each case two adjacent groups $R^{8a}$, $R^{8b}$, $R^{8c}$, $R^{8d}$ may form a cyclic ketal or acetal group or a 1,2-di($C_{1-3}$-alkoxy)-1,2-di($C_{1-3}$-alkyl)-ethylene bridge, while the above-mentioned ethylene bridge forms a substituted dioxane ring together with two oxygen atoms and the associated two carbon atoms of the pyranose ring, and while alkyl, aryl and/or benzyl groups may be mono- or polysubstituted by halogen or $C_{1-3}$-alkoxy, and while benzyl groups may also be substituted by a di-($C_{1-3}$-alkyl)amino group; and $R^a$, $R^b$, $R^c$ independently of one another represent $C_{1-4}$-alkyl, aryl or aryl-$C_{1-3}$-alkyl, while the alkyl or aryl groups may be mono- or polysubstituted by halogen;

while by the aryl groups mentioned in the definition of the above groups are meant phenyl or naphthyl groups, preferably phenyl groups;

and $R^1$ to $R^5$, $R^6$, $R^{7a}$, $R^{7b}$, $R^{7c}$ have the meanings given in claim 1, is hydrolysed, and optionally a compound of general formula I thus obtained wherein $R^6$ denotes a hydrogen atom is converted by acylation into a corresponding acyl compound of general formula I, and/or if necessary any protective group used in the reactions described above is cleaved and/or optionally a compound of general formula I thus obtained is resolved into its stereoisomers and/or optionally a compound of general formula I thus obtained is converted into the salts thereof, particularly for pharmaceutical use into the physiologically acceptable salts thereof.

16. A compound of general formula IV

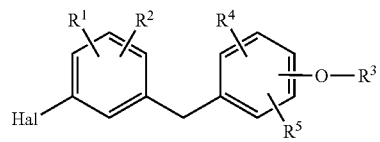

wherein Hal denotes chlorine, bromine or iodine and the groups $R^1$, $R^2$, $R^3$, $R^4$ and $R^5$ are defined as in claim 1.

17. A compound of formula IV according to claim 16, characterised by the formula

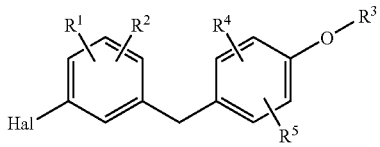

wherein Hal denotes chlorine, bromine or iodine and the groups $R^1$, $R^2$, $R^4$ and $R^5$ are defined as in claim 1.

18. A compound of general formula II

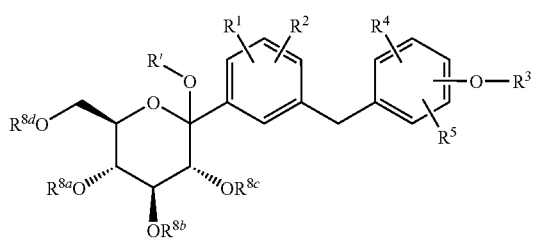

wherein $R'$ denotes H, $C_{1-4}$-alkyl, ($C_{1-18}$-alkyl)carbonyl, ($C_{1-18}$-alkyl)oxycarbonyl, arylcarbonyl and aryl-($C_{1-3}$-alkyl)-carbonyl, wherein the alkyl or aryl groups may be mono- or polysubstituted by halogen;

$R^{8a}$, $R^{8b}$, $R^{8c}$, $R^{8d}$ independently of one another have one of the meanings given for the groups $R^6$, $R^{7a}$, $R^{7b}$, $R^{7c}$, or denote a benzyl group or a $R^a R^b R^c Si$ group or a ketal or acetal group, while in each case two adjacent groups $R^{8a}$, $R^{8b}$, $R^{8c}$, $R^{8d}$ may form a cyclic ketal or acetal group or a 1,2-di($C_{1-3}$-alkoxy)-1,2-di ($C_{1-3}$-alkyl)-ethylene bridge, while the above-mentioned ethylene bridge forms, together with two oxygen atoms and the two associated carbon atoms of the pyranose ring, a substituted dioxane ring, and while alkyl, aryl and/or benzyl groups may be mono- or polysubstituted by halogen or $C_{1-3}$-alkoxy, and while benzyl groups may also be substituted by a di-($C_{1-3}$-alkyl)amino group; and $R^a$, $R^b$, $R^c$ independently of one another denote $C_{1-4}$-alkyl, aryl or aryl-$C_{1-3}$-alkyl, while the alkyl or aryl groups may be mono- or polysubstituted by halogen;

while by the aryl groups mentioned in the definition of the above groups are meant phenyl or naphthyl groups, preferably phenyl groups;

and $R^1$ to $R^5$ are defined as in claim 1.

\* \* \* \* \*